Figure 1:
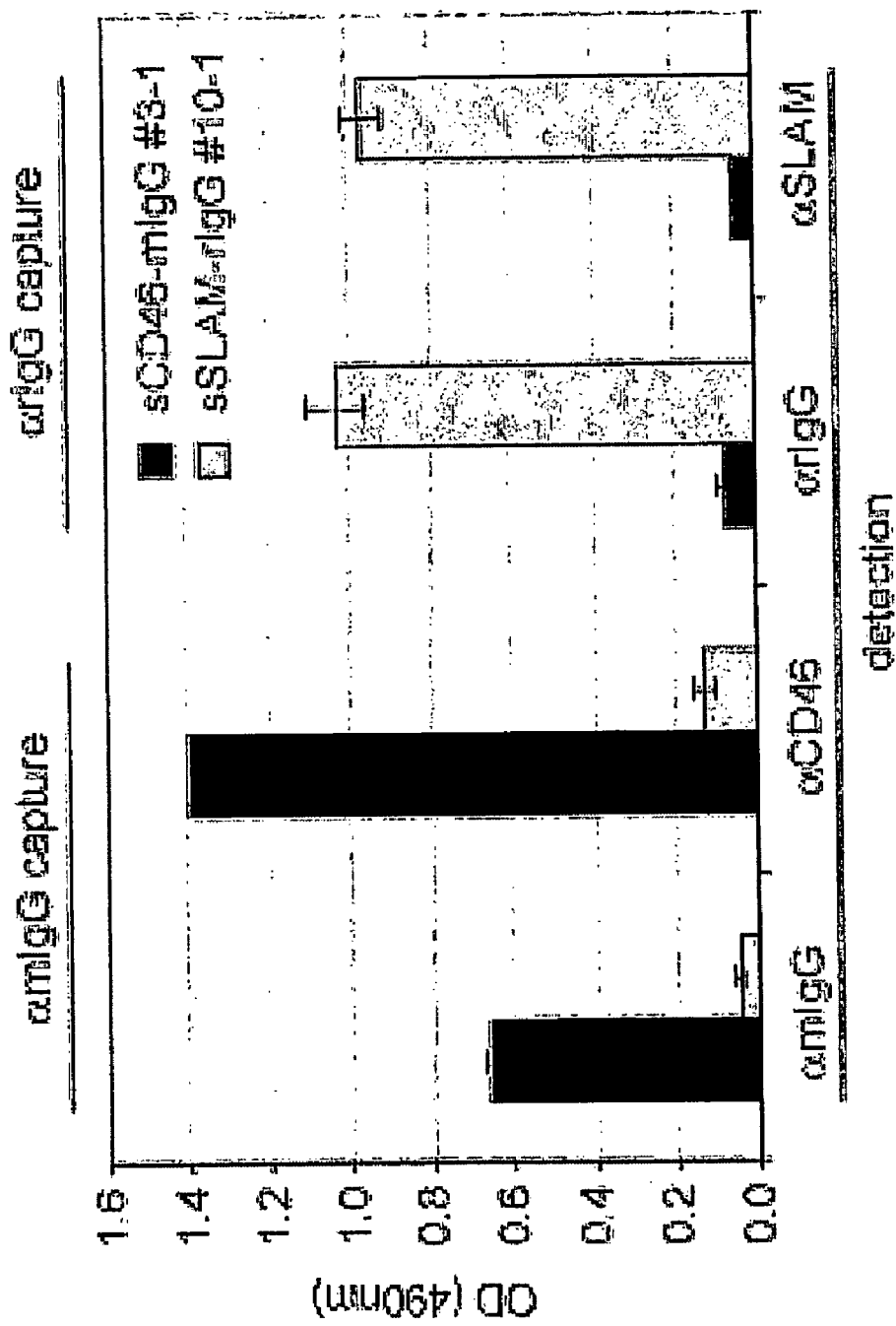

US007635752B2

(12) United States Patent
Cattaneo et al.

(10) Patent No.: US 7,635,752 B2
(45) Date of Patent: Dec. 22, 2009

(54) ABLATED SLAM-DEPENDENT ENTRY

(75) Inventors: Roberto Cattaneo, Rochester, MN (US); Sompong Vongpunsawad, Rochester, MN (US); Stephen J. Russell, Rochester, MN (US); Takafumi Nakamura, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 522 days.

(21) Appl. No.: 10/512,627

(22) PCT Filed: May 2, 2003

(86) PCT No.: PCT/US03/13679

§ 371 (c)(1),
(2), (4) Date: May 25, 2005

(87) PCT Pub. No.: WO03/093431

PCT Pub. Date: Nov. 13, 2003

(65) Prior Publication Data

US 2005/0271621 A1 Dec. 8, 2005

Related U.S. Application Data

(60) Provisional application No. 60/377,681, filed on May 3, 2002.

(51) Int. Cl.
*C07K 14/12* (2006.01)
*A

OTHER PUBLICATIONS

Cocks et al., "A novel receptor involved in T-cell activation," *Nature*, 1995, 376:260-263.

Devaux et al., "CD46 Short Consensus Repeats III and IV Enhance Measles Virus Binding but Impair Soluble Hemagglutinin Binding," *J. Virol.*, 1997, 71(5):4157-4160.

Duclos and Ward, "Measles Vaccines—A Review of Adverse Events," *Drug Safety*, 1998, 19(6):435-454.

Federspiel and Hughes, "Retroviral Gene Delivery," *Methods in Cell Biology*, 1998, 52:179-214.

Galanis et al., "Use of Viral Fusogenic Membrane Glycoproteins as Novel Therapeutic Transgenes in Gliomas," *Human Gene Therapy*, 2001, 12:811-821.

Griffin and Bellini, "Measles Virus," *Fields Virology*, 1996; pp. 1267-1312, Fields et al. (eds.), Lippincott—Raven Publishers, New York.

Grote et al., "Live attenuated measles virus induce regression of human lymphoma xenografts in immunodeficient mice," *Blood*, 2001, 97(12):3746-3754.

Hammond et al., "Single-Chain Antibody Displayed on a Recombinant Measles Virus Confers Entry through the Tumor-Associated Carcinoembryonic Antigen," *J. Virol.*, 2001, 75(5):2087-2096.

Hourcade et al., "Analysis of the Human Regulators of Complement Activation (RCA) Gene Cluster with Yeast Artificial Chromosomes (YACs)," *Genomics*, 1992, 12:289-300.

Hsu et al., "A Single Amino Acid Change in the Hemagglutinin Protein of Measles Virus Determines Its Ability to Bind CD46 and Reveals Another Receptor on Marmoset B Cells," *J. Virol.*, 1998, 72(4):2905-2916.

Hsu et al., "Use of Site-Specific Mutagenesis and Monoclonal Antibodies to Map Regions of CD46 That Interact with Measles Virus H Protein," *Virology*, 1999, 258:314-326.

Hu et al., "Characterization of a region involved in binding of measles virus H protein and its receptor SLAM (CD150)," *Biochem. Biophys. Res. Commun.*, 2004, 316:698-704.

Lecouturier et al., "Identification of Two Amino Acids in the Hemagglutinin Glycoprotein of Measles Virus (MV) That Govern Hemadsorption, HeLa Cell Fusion, and CD46 Downregulation: Phenotypic Markers That Differentiate Vaccine and Wild-Type MV Strains," *J. Virol.*, 1996, 70 (7):4200-4204.

Linardakis et al., "Regulated Expression of Fusogenic Membrane Glycoproteins," *Gene Therapy*, 1999, 6(1):S4, abstract 13.

Martin et al., "Studies of the binding properties of influenza hemagglutinin receptor-site mutants," *Virology*, 1998, 241(1):101-111.

Mori et al., "A novel amino acid substitution at the receptor-binding site on the hemagglutinin of H3N2 influenza A viruses isolated from 6 cases with acute encephalopathy during the 1997-1998 season in Tokyo," *Arch. Virol.*, 1999, 144(1):147-155.

Mrkic et al., "Measles Virus Spread and Pathogenesis in Genetically Modified Mice," *J. Virol.*, 1998, 72(9):7420-7427.

Nies and Spielberg, "Principles of Therapeutics," *The Pharmacological Basis of Therapeutics*, 1996, Chapter 3, pp. 43-62.

Nussbaum et al., "Functional and Structural Interactions between Measles Virus Hemagglutinin and CD46," *J. Virol.*, 1995, 69(6):3341-3349.

Patterson et al., "Structural and Functional Studies of the Measles Virus Hemagglutinin: Identification of a Novel Site Required for CD46 Interaction," *Virology*, 1999, 256:142-151.

Peng et al., "Systemic therapy of myeloma xenografts by an attenuated measles virus," *Blood*, 2001, 98(7):2002-2007.

Peng et al., "Oncolytic measles viruses displaying a single-chain antibody against CD38, a myeloma cell marker," *Blood*, 2003, 101(7):2557-2562.

Radecke et al., "Rescue of measles viruses from cloned DNA," *EMBO J.*, 1995, 14(23):5773-5784.

Schneider et al., "Efficiency of Measles Virus Entry and Dissemination through Different Receptors," *J. Virol.*, 2002, 76(15):7460-7467.

Schneider et al., "Recombinant Measles Viruses Efficiently Entering Cells through Targeted Receptors," *J. Virol.*, 2000, 74(21):9928-9936.

Steinhauer et al., "Studies using double mutants of the conformational transitions in influenza hemagglutinin required for its membrane fusion activity," *Proc. Natl. Acad. Sci. USA*, 1996, 93(23):12783-12788.

Sutter et al., "Non-replicating vaccinia vector efficiently expresses bacteriophage T7 RNA polymerase," *FEMS Lett.*, 1995, 371:9-12.

Tatsuo et al., "Morbilliviruses Use Signaling Lymphocyte Activation Molecules (CD150) as Cellular Receptors," *J. Virol.*, 75(13):5842-5850.

Tatsuo et al., "SLAM (CDw150) is a cellular receptor for measles virus," *Nature*, 2000, 406:893-897.

Jin et al., "Genetic and antigenic characterisation of the haemagglutinin protein of measles virus strains recently circulating in the UK," *Virus Research*, 1998, 55:107-113.

Takeuchi et al., "Recombinant wild-type and Edmonston strain measles viruses bearing heterologous H proteins: Role of H protein in cell fusion and host cell specificity," *J. Virol.*, 2002, 76(10):4891-4900.

\* cited by examiner

Figure 3

Figure 4

```
        1           3b  4b                5  6         7b 8b                10b       11b
        ‾‾          ‾‾  ‾‾                ‾  ‾         ‾‾ ‾‾                ‾‾‾       ‾‾‾
        SAA   2 3a  4a                    5  6         7a 8a    9    10a             11a
              ‾  ‾‾  ‾‾                   ‾  ‾         ‾‾ ‾‾    ‾    ‾‾‾             ‾‾‾
              AA SASS AASA                SAAAAS       ASA ASA  ASA  SAAS            AA·A
MV      CFQQACKGKIQALCENPEWAPLKDNRIPSYGVLSVDLSLTVELKIKIASGFGPLITHGSG                  440
CDV        ·LES··QR·TYPM·NQAS·E·FGGRQL····R·TLP·DAS·D·QLN·SFTY··V·LN·D·

13b                                         20b
                    ‾‾‾                                         ‾‾‾
        12   13a 14              15  16    17 18          19   20a    21    22  23
        ‾‾   ‾‾‾ ‾‾              ‾‾  ‾‾    ‾‾ ‾‾          ‾‾   ‾‾‾    ‾‾    ‾‾  ‾‾
        S·A  AAA SA              SAAASSA   ASASSSA        ASA  SSSA   SAAA  AS  AAS
MV      MDLYKSNHNNVYWLTIPPMKNLALGVINTLEWIPRFKVSPYLFTVPIKEAGEDCHAPTYL                  500
CDV     ···Y·E·PLL·SG······KDGTIS·L··KAGRGDQ·T·L·HVL·FAPR·SSGN·YL·IQT 24                25 26     27         28           29  30  31    32
        ‾‾                ‾‾ ‾‾     ‾‾         ‾‾           ‾‾  ‾‾  ‾‾    ‾‾
        SSAS              ASA S·S   ASA        SA           A·A AS  SA    SS
MV      PAEVDGDVKLSSNLVILPGQDLQYVLATYDTSRVEHAVVYYYSPSRSFSYFYPFRLPIK                   560
CDV     SQIR·R··LIE··I·V··T·SIR··I····I··SD··I····D·I·TI··TH····TT·

33  34              35    36  STOP(583)
        ‾‾  ‾‾              ‾‾    ‾‾
        SA  AS              AA    AA
MV      GVPIELQVECFTWDQKLWCRHFCVLADSESGGHITHSGMVGMVSCTVTREDGTNRR                      617
CDV     ·R·DF·RI···V··DN···HQ·YRFEADIANSTTSVENL·RIRF··NR
```

Figure 5

```
                                            408-411                           432-433  440-442
                                             S·AA                               AS       A     440
MV   CFQQACKGKIQALCENPEWAPLKDNRIPSYGVLSVDLSLTVELKIKIASGFGPLITHGSG
RV   ·RRE··RE·PPPF·NSTD·E·LEAGRI·A··I·TIR·GLADK·KLT·ISEF··L·THDS·
CDV  ·LES··QR·TYPM·NQAS·E·FGGRQL·S··R·TLP·DASVD·QLN·SFTY··V·LNGD·

456-458
                    454-456
                    SASSS
     SA
MV   MDLYKSNHNNVYWLTIPPMKNLALGVINTLEWIPRFKVSPYLFTVPIKEAGEDCHAPTYL    500
RV   ··L·TPLDG·EY······LQNSAL·TV·TLVLEPSLKIS·NIL·LPIRSGGGD·YT·TYL
CDV  ··Y·ESPLL·SG······KDGTIS·LI·KAGRGDQFTVL·HVL·FAPRESSGN·YL·IQT 517-518        529-530   539-541
        512-513      527-528  532-533   536-537            550-551   560-561
     507-508    524-525   AS  SAA                                       A       560
     AS   AA   SS  AS SAAA AA                                           AA
MV   PAEVDGDVKLSSNLVILPGQDLQYVLATYDTSRVEHAVVYYVSPSRSFSYFYPFRLPIK
RV   SDLA·D··KLS··L·I··SRNLQ··S·····T··VE··I····I·SAG·LS··YY·VK·PI·
CDV  SQIR·R··LIE··I·V··TQSIR··I·····I··SD··I····V·DPI·TI··TH·FR·TT·

A                                                                         617
MV   GVPIELQVECFTWDQKLWCRHFC-VLADSESGGHITHSGMVGMGVSCTVTREDGTNRR
RV   ·D·VS·QIG··P·GLK···HH·C-SVI·SGTRKQVTHTGA·GIEIT------·S·------
CDV  ·R·DF·RIE··V·DDN···HQ·YRFEA·IAN-STTSVENL·RIRFS-------------
```

Figure 7A

```
MSPQRDRINAFYKDNPHPKGSRIVINREHLMIDRPYVLLAVLFVMFLSLIGLLAIAGIRL    60
HRAAIYTAEIHKSLSTNLDVTNSIEHQVKDVLTPLFKIIGDEVGLRTPQRFTDLVKFISD   120
KIKFLNPDREYDFRDLTWCINPPERIKLDYDQYCADVAAEELMNALVNSTLLETRTTNQF   180
LAVSKGNCSGPTTIRGQFSNMSLSLLDLYLGRGYNVSSIVTMTSQGMYGGTYLVEKPNLS   240
SKRSELSQLSMYRVFEVGVIRNPGLGAPVFHMTNYLEQPVSNDLSNCMVALGELKLAALC   300
HGEDSITIPYQGSGKGVSFQLVKLGVWKSPTDMQSWVPLSTDDPVIDRLYLSSHRGVIAD   360
NQAKWAVPTTRTDDKLRMETCFQQACKGKIQALCENPEWAPLKDNRIPSYGVLSVDLSLT   420
VELKIKIASGFGPLITHGSGMDLYKSNHNNVYWLTIPPMKNLALGVINTLEWIPRFKVSP   480
YLFNVPIKEAGEDCHAPTYLPAEVDGDVKLSSNLVILPGQDLQYVLATYDTSRVEHAVVY   540
YVYSPSRSFSYFYPFRLPIKGVPIELQVECFTWDQKLWCRHFCVLADSESGGHITHSGME   600
GMGVSCTVTREDGTNRR                                             617
(SEQ ID NO:1)
```

Figure 7B

```
MLSYQDKVGAFYKDNARANSTKLSLVTEEHGGRRPPYLLFVLLILLVGILALLAITGVRF    60
HQVSTSNMEFSRLLKEDMEKSEAVHHQVIDVLTPLFKIIGDEIGLRLPQKLNEIKQFILQ   120
KTNFFNPNREFDFRDLHWCINPPSKVKVNFTNYCESIGIRKAIASAANPILLSALSGGRS   180
DIFPPHRCSGATTSVGKVFPLSVSLSMSLISRTSEIINMLTAISDGVYGKTYLLVPDDIE   240
REFDTQEIRVFEIGFIKRWLNDMPLLQTTNYMVLPENSKAKVCTIAVGELTLASLCVEES   300
TVLLYHDSSGSQDGILVVTLGIFWATPMDHIEEVIPVAHPSMEKIHITNHRGFIKDSIAT   360
WMVPALASEKQEEQKGCLESACQRKTYPMCNQTSWEPFGGRQLPSYGRLTLPLDASVDLQ   420
LNISFTYGPVILNGDGMDYYESPLLNSGWLTIPPKNGTIVGLINKAGRGDQFTVLPHVLT   480
FAPWESSGNCYLPIQTSQIIDRDVLIESNIVVLPTQSFRYVIATYDISRSDHAIVYYVYD   540
PIRTISYTHPFRLTTKGRPDFLRIECFVWDDNLWCHQFYRFEADIANSTTSVENLVRIRF   600
SCNR                                                          604
(SEQ ID NO:2)
```

Figure 7C

```
MSSPRDRVNAFYKDNLQFKNTRVVLNKEQLLIERPYMLLAVLFVMFLSLVGLLAIAGIRL    60
HRAAVNTAEINSGLTTSIDITKSIEYQVKDVLTPLFKIIGDEVGLRTPQRFTDLTKFISD   120
KIKFLNPDKEYDFRDINWCISPPERIKINYDQYCAHTAAEELITMLVNSSLAGTSVLPTS   180
LVNLGRSCTGSTTTKGQFSNMSLALSGIYSGRGYNISSMITITEKGMYGSTYLVGKHNQG   240
ARRPSTAWQRDYRVFEVGIIRELGLGTPVFHMTNYLELPRQPELEICMLALGEFKLAALC   300
LADNSVALHYGGLRDDHKIRFVKLGVWPSPADSDTLATLSAVDPTLDGLYITTHRGIIAA   360
GKAVWVVPVTRTDDQRKMGQCRREACREKPPPFCNSTDWEPLEAGRIPAYGILTIRLGLA   420
DKLKLTIISEFGPLITHDSGMDLYTPLDGNEYWLTIPPLQNSALGTVNTLVLEPSLKISP   480
NILTLPIRSGGGDCYTPTYLSDLADDDVKLSSNLVILPSRNLQYVSATYDTSRVEHAIVY   540
YIYSAGRLSSYYYPVKLPIKGDPVSLQIGCFPWGLKLWCHHFCSVIDSGTRKQVTHTGAV   600
GIEITCNSR.QCLGPTRSRRPGPPTAVGPGTALHHADSFQYYHY                  644
(SEQ ID NO:3)
```

Figure 8

```
MSIMGLKVNVSAIFMAVLLTLQTPTGQIHWGNLSKIGVVGIGSASYKVMTRSSHQSLVIK    60
LMPNITLLNNCTRVEIAEYRRLLRTVLEPIRDALNAMTQNIRPVQSVASSRRHKRFAGVV   120
LAGAALGVATAAQITAGIALHQSMLNSQAIDNLRASLETTNQAIEAIRQAGQEMILAVQG   180
VQDYINNELIPSMNQLSCDLIGQKLGLKLLRYYTEILSLFGPSLRDPISAEISIQALSYA   240
LGGDINKVLEKLGYSGGDLLGILESRGIKARITHVDTESYFIVLSIAYPTLSEIKGVIVH   300
RLEGVSYNIGSQEWYTTVPKYVATQGYLISNFDESSCTFMPEGTVCSQNALYPMSPLLQE   360
CLRGSTKSCARTLVSGSFGNRFILSQGNLIANCASILCKCYTTGTIINQDPDKILTYIAA   420
DHCPVVEVNGVTIQVGSRRYPDAVYLHRIDLGPPISLERLDVGTNLGNAIAKLEDAKELL   480
ESSDQILRSMKGLSSTSIVYILIAVCLGGLIGIPALICCCRGRCNKKGEQVGMSRPGLKP   540
DLTGTSKSYVRSL                                                 553
(SEQ ID NO:8)
```

FIGURE 9A

```
ATGTCACCACAACGAGACCGGATAAATGCCTTCTACAAAGATAACCCCCATCCCAAGGGA     60
AGTAGGATAGTCATTAACAGAGAACATCTTATGATTGATAGACCTTATGTTTTGCTGGCT    120
GTTCTGTTTGTCATGTTTCTGAGCTTGATCGGGTTGCTAGCCATTGCAGGAATTCGACTT    180
CATCGGGCAGCCATCTACACCGCAGAGATCCATAAAAGCCTCAGCACCAATCTAGATGTA    240
ACTAACTCAATCGAGCATCAGGTCAAGGACGTGCTGACACCACTCTTCAAAATCATCGGT    300
GATGAAGTGGGCCTGAGGACACCTCAGAGATTCACTGACCTAGTGAAATTCATCTCTGAC    360
AAGATTAAATTCCTTAATCCGGATAGGGAGTACGACTTCAGAGATCTCACTTGGTGTATC    420
AACCCGCCAGAGAGAATCAAATTGGATTATGATCAATACTGTGCAGATGTGGCTGCTGAA    480
GAGCTCATGAATGCATTGGTGAACTCAACTCTACTGGAGACCAGAACAACCAATCAGTTC    540
CTAGCTGTCTCAAAGGGAAACTGCTCAGGGCCCACTACAATCAGAGGTCAATTCTCAAAC    600
ATGTCGCTGTCCCTGTTAGACTTGTATTTAGGTCGAGGTTACAATGTGTCATCTATAGTC    660
ACTATGACATCCCAGGGAATGTATGGGGAACTTACCTAGTGGAAAAGCCTAATCTGAGC    720
AGCAAAAGGTCAGAGTTGTCACAACTGAGCATGTACCGAGTGTTTGAAGTAGGTGTTATC    780
AGAAATCCGGGTTTGGGGGCTCCGGTGTTCCATATGACAAACTATCTTGAGCAACCAGTC    840
AGTAATGATCTCAGCAACTGTATGGTGGCTTTGGGGGAGCTCAAACTCGCAGCCCTTTGT    900
CACGGGGAAGATTCTATCACAATTCCCTATCAGGGATCAGGGAAAGGTGTCAGCTTCCAG    960
CTCGTCAAGCTAGGTGTCTGGAAATCCCCAACCGACATGCAATCCTGGGTCCCCTTATCA   1020
ACGGATGATCCAGTGATAGACAGGCTTTACCTCTCATCTCACAGAGGTGTTATCGCTGAC   1080
AATCAAGCAAAATGGGCTGTCCCGACAACACGAACAGATGACAAGTTGCAATGGAGACA   1140
TGCTTCCAACAGGCGTGTAAGGGTAAAATCCAAGCACTCTGCGAGAATCCCGAGTGGGCA   1200
CCATTGAAGGATAACAGGATTCCTTCATACGGGGTCTTGTCTGTTGATCTGAGTCTGACA   1260
GTTGAGCTTAAAATCAAAATTGCTTCGGGATTCGGGCCATTGATCACACACGGTTCAGGG   1320
ATGGACCTATACAAATCCAACCACAACAATGTGTATTGGCTGACTATCCCGCCAATGAAG   1380
AACCTAGCCTTAGGTGTAATCAACACATTGGAGTGGATACCGAGATTCAAGGTTAGTCCC   1440
TACCTCTTCAATGTCCCAATTAAGGAAGCAGGCGAAGACTGCCATGCCCCAACATACCTA   1500
CCTGCGGAGGTGGATGGTGATGTCAAACTCAGTTCCAATCTGGTGATTCTACCTGGTCAA   1560
GATCTCCAATATGTTTTGGCAACCTACGATACTTCCAGGGTTGAACATGCTGTGGTTTAT   1620
TACGTTTACAGCCCAAGCCGCTCATTTTCTTACTTTTATCCTTTTAGGTTGCCTATAAAG   1680
GGGGTCCCCATCGAATTACAAGTGGAATGCTTCACATGGGACCAAAAACTCTGGTGCCGT   1740
CACTTCTGTGTGCTTGCGGACTCAGAATCTGGTGGACATATCACTCACTCTGGGATGGAG   1800
GGCATGGGAGTCAGCTGCACAGTCACCCGGGAAGATGGAACCAATCGCAGATAG         1854
(SEQ ID NO:9)
```

FIGURE 9B

```
ATGCTCTCCTACCAAGACAAGGTGGGTGCCTTCTACAAGGATAATGCAAGAGCCAATTCA    60
ACCAAGCTGTCCTTAGTGACAGAAGAACATGGGGGCAGGAGACCACCTTATTTGTTGTTT   120
GTCCTTCTCATCTTATTGGTTGGAATCCTGGCCTTGCTTGCTATCACTGGAGTTCGATTT   180
CACCAAGTATCAACTAGCAATATGGAATTTAGCAGATTGCTGAAAGAGGATATGGAGAAA   240
TCAGAGGCCGTACATCACCAAGTCATAGATGTCTTGACACCGCTCTTCAAGATTATTGGA   300
GATGAGATTGGGTTACGGTTGCCACAAAAGCTAAACGAGATCAAACAATTTATCCTTCAA   360
AAGACAAATTTCTTCAATCCGAACAGAGAATTCGACTTCCGCGATCTCCACTGGTGCATT   420
AACCCGCCTAGTAAGGtCAAGGTGAATTTTACTAATTACTGtGAGTCAATTGGGATCAGA   480
AAAGCTATTGCATCGGCAGCAAATCCTATCCTTTTATCAGCCCTATCTGGGGGCAGAAGT   540
GACATATTCCCACCACACAGATGCAGTGGAGCTACTACTTCAGTAGGCAAAGTTTTCCCC   600
CTATCAGTCTCATTATCCATGTCTTTGATCTCAAGAACCTCAGAGATAATCAATATGCTG   660
ACCGCTATCTCAGACGGCGTGTATGGCAAAACTTACTTGCTAGTGCCTGATGATATAGAA   720
AGAGAGTTCGACACTCAAGAGATTCGAGTCTTTGAAATAGGGTTCATCAAAAGGTGGCTG   780
AATGACATGCCATTACTCCAAACAACCAACTATATGGTACTCCGGAGAATTCCAAAGCC   840
AAGGTATGTACTATAGCAGTGGGTGAGTTGACACTGGCTTCCTTGTGTGTAGAAGAGAGC   900
ACTGTATTATTATATCATGACAGCAGTGGTTCACAAGATGGTATTCTAGTAGTGACACTG   960
GGGATATTTTGGGCAACACCTATGGATCACATTGAGGAAGTGATACCTGTCGCTCACCCA  1020
TCAATGGAGAAAATACATATAACAAACCACCGTGGTTTTATAAAAGATTCAATTGCAACC  1080
TGGATGGTGCCTGCCCTGGCCTCTGAGAAACAAGAAGAACAAAAAGGTTGTCTGGAGTCA  1140
GCTTGTCAAAGAAAAACCTACCCCATGTGCAACCAAACGTCATGGGAACCCTTCGGAGGA  1200
AGACAGTTGCCATCTTATGGGCGGTTGACATTACCTCTAGATGCAAGTGTTGACCTTCAA  1260
CTTAACATATCGTTCACATACGGTCCGGTCATACTGAATGGAGATGGTATGGATTATTAT  1320
GAAAGCCCACTTTTGAACTCCGGATGGCTTACCATTCCTCCCAAAAACGGAACAATCGTT  1380
GGATTGATAAACAAAGCAGGTAGAGGAGACCAGTTCACTGTACTCCCCATGTGTTAACA  1440
TTTGCGCCTTGGGAATCAAGTGGAAATTGTTATTTACCTATTCAAACATCTCAAATTATA  1500
GATAGAGATGTCCTCATTGAGTCCAATATAGTGGTGTTGCCTACACAGAGTTTTAGATAT  1560
GTCATAGCAACGTATGACATATCACGAAGTGATCATGCGATTGTTTATTATGTTTATGAC  1620
CCAATCCGGACGATTTcTTATACGCACCCATTTAGACTAACTACCAAGGGTAGACCTGAT  1680
TTCCTAAGGATTGAATGTTTTGTGTGGGATGACAATTTGTGGTGTCACCAATTTTACAGA  1740
TTCGAGGCTGACATCGCCAACTCTACAACCAGTGTTGAGAATTTAGTCCGTATAAGATTC  1800
TCATGTAACCGTTAA                                                1815
(SEQ ID NO:10)
```

FIGURE 9C

```
AGGATGCAAGATCATCCACCATGTCCTCCCCAAGAGACAGGGTCAATGCCTTCTACAAAG     60
ACAACCTCCAATTTAAGAACACTCGAGTGGTTCTTAATAAAGAGCAGCTCCTGATAGAAA    120
GGCCTTACATGTTGCTGGCGGTGCTGTTTGTTATGTTCCTGAGCCTAGTGGGGCTGTTGG    180
CCATTGCAGGTATCAGACTCCACCGAGCTGCTGTCAACACAGCAGAGATCAACAGTGGTC    240
TGACGACAAGCATTGATATTACCAAGTCTATTGAGTACCAGGTCAAGGACGTCTTAACTC    300
CCCTCTTCAAAATAATTGGAGATGAGGTCGGGCTGAGGACACCTCAGAGATTCACAGATC    360
TGACTAAATTCATATCAGACAAGATTAAGTTCCTTAACCCTGATAAAGAGTACGACTTCA    420
GGGATATTAACTGGTGCATCAGTCCCCAGAGAGAATCAAGATTAATTATGATCAGTATT    480
GTGCTCACACAGCTGCTGAGGAGCTGATAACTATGCTGGTCAATTCGTCTCTGGCAGGTA    540
CTTCGGTACTACCGACATCATTAGTCAACTTGGGGAGGAGCTGTACCGGGTCCACAACGA    600
CTAAAGGTCAATTCTCTAACATGTCATTGGCTCTTTCAGGGATATACTCAGGTCGTGGCT    660
ACAATATTTCATCCATGATAACAATCACTGAGAAAGGCATGTACGGAAGCACTTATCTAG    720
TCGGGAAACATAATCAGGGAGCCAGGAGGCCAAGCACTGCTTGGCAACGGGATTACCGAG    780
TCTTTGAAGTAGGCATAATTAGAGAACTAGGACTGGGCACACCAGTGTTTCATATGACAA    840
ACTACCTGGAGCTCCCAAGACAGCCGGAATTGGAGATCTGCATGCTAGCTCTAGGAGAGT    900
TCAAATTAGCTGCCCTCTGCTTAGCTGATAACTCTGTCGCACTGCATTACGGGGGGTTAA    960
GGGACGACCACAAGATCAGGTTTGTCAAACTGGGAGTATGGCCATCACCAGCCGACTCAG   1020
ACACCCTGGCCACTCTTTCAGCAGTAGATCCGACCTTGGATGGGCTCTATATCACAACTC   1080
ATAGGGGAATCATAGCTGCAGGGAAGGCCGTATGGGTCGTCCCTGTGACGAGAACAGATG   1140
ACCAAAGGAAAATGGGACAGTGCCGCCGAGAGGCTTGTCGAGAGAAACCACCACCTTTCT   1200
GTAACAGTACAGATTGGGAGCCATTAGAGGCCGGCCGTATACCGGCATATGGAATACTAA   1260
CTATCAGGCTGGGGCTGGCTGATAAGCTGAAATTGACCATAATTTCAGAATTTGGTCCCT   1320
TGATCACACATGACTCAGGGATGGACTTATACACCCCACTTGACGGTAATGAGTACTGGC   1380
TGACTATTCCTCCATTGCAGAATTCAGCTTTAGGAACGGTGAACACCCTAGTTTTAGAGC   1440
CCAGTCTCAAAATTAGTCCTAACATCCTTACTCTCCCCATCAGGTCGGGGGAGGTGACT   1500
GTTACACTCCCACTTACCTGTCAGACCTGGCCGATGATGATGTTAAACTGAGCTCCAATC   1560
TTGTAATCCTCCCGAGTAGAAACCTCCAATATGTGTCAGCAACCTACGACACCTCTAGAG   1620
TTGAGCATGCCATTGTATACTATATCTATAGCGCCGGGCGACTATCATCGTATTACTACC   1680
CTGTTAAGTTGCCCATAAAGGGAGATCCTGTCAGCCTGCAGATAGGATGCTTCCCTTGGG   1740
GCCTCAAGCTATGGTGCCATCATTTCTGCTCTGTTATAGATTCAGGAACTCGCAAGCAGG   1800
TCACCCATACAGGGGCAGTAGGGATTGAGATCACTTGCAATAGCAGATAGCAGTGTCTTG   1860
GCCCTACAAGATCTCGGAGACCGGGACCCCAACAGCTGTGGGACCAGGCACCGCGCTGC   1920
ACCATGCAGACAGCTTTCAATATTACCATTAT                                1952
(SEQ ID NO:11)
```

Figure 10
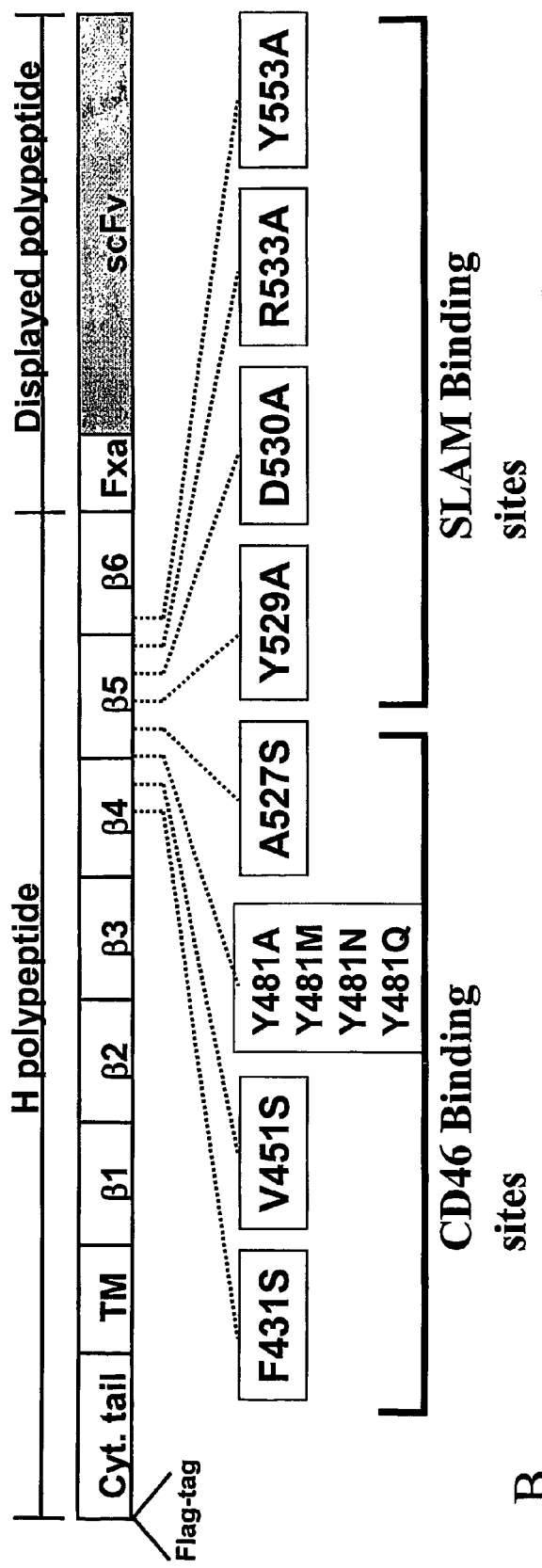
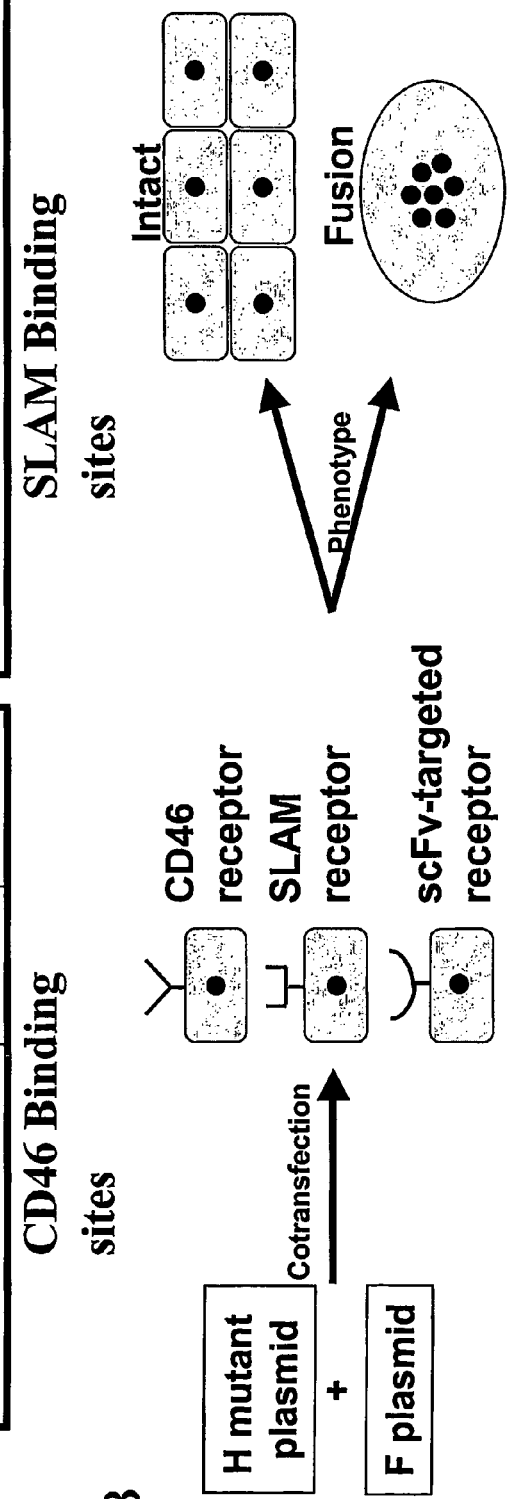

Figure 11

The number of syncytia and of nuclei per the syncytium

| H polypeptide | Syncytial counts# | | | Nuclei / syncytium* | | |
|---|---|---|---|---|---|---|
| | Vero | CHO-SLAM | CHO-CD38 | Vero | CHO-SLAM | CHO-CD38 |
| Edm | 3086±122 | 2886±31 | 0 | +++ | +++ | – |
| Edm-CD38 | 0 | 0 | 2334±136 | +++ | +++ | +++ |
| Edm431S,451S,481N,529A,530A,533A,553A-CD38 | 0 | 0 | 0 | – | – | – |
| Edm431S,451S,481N,527S,529A,530A,533A,553A-CD38 | 0 | 0 | 0 | – | – | – |
| Edm431S,451S,481N-CD38 | 0 | 0 | 0 | – | – | – |
| Edm431S,451S,481N,527S-CD38 | 0 | 0 | 801±97.0 | ± | – | + |
| Edm529A,530A,533A,553A-CD38 | 171±38.0 | 0 | 0 | ± | – | – |
| Edm431S-CD38 | 43.9±18.7 | 1890±136 | 625±117 | ± | ++ | + |
| Edm451S-CD38 | 2417±209 | 2520±448 | 928±122 | +++ | +++ | + |
| Edm481N-CD38 | 19.5±15.9 | 1538±285 | 723±140 | ± | ++ | + |
| Edm527S-CD38 | 0 | 0 | 0 | – | – | – |
| Edm431S,529A,530A,533A,553A-CD38 | 0 | 0 | 0 | – | – | – |
| Edm451S,529A,530A,533A,553A-CD38 | 151±51.4 | 0 | 791±111 | ± | – | + |
| Edm481N,529A,530A,533A,553A-CD38 | 0 | 0 | 0 | – | – | – |
| Edm431S,529A-CD38 | 0 | 0 | 0 | – | – | – |
| Edm431S,530A-CD38 | 0 | 0 | 0 | – | – | – |
| Edm431S,533A-CD38 | 0 | 0 | 645±47.0 | – | – | + |
| Edm431S,553A-CD38 | 0 | 0 | 0 | – | – | – |
| Edm451S,529A-CD38 | 0 | 0 | 972±134 | – | – | + |
| Edm451S,530A-CD38 | 1416±121 | 0 | 933±109 | ++ | – | + |
| Edm451S,533A-CD38 | 1465±180 | 0 | 1255±81.9 | ++ | – | + |
| Edm451S,553A-CD38 | 166±49.2 | 0 | 820±112 | ± | – | + |
| Edm481N,529A-CD38 | 0 | 0 | 0 | – | – | – |
| Edm481N,530A-CD38 | 0 | 0 | 0 | – | – | – |
| Edm481N,533A-CD38 | 0 | 0 | 981±179 | – | – | + |
| Edm481N,553A-CD38 | 0 | 0 | 0 | – | – | – |
| Edm481A,533A-CD38 | 0 | 0 | 2705±147 | – | – | +++ |
| Edm481M,533A-CD38 | 0 | 0 | 1899±300 | – | – | ++ |
| Edm481Q,533A-CD38 | 0 | 0 | 1191±131 | – | – | + |

US 7,635,752 B2

ABLATED SLAM-DEPENDENT ENTRY

RELATED APPLICATIONS

This application is a National Stage application under 35 U.S.C. §371 of international application PCT/US03/13679, filed May 2, 2003, which claims the benefit of U.S. Provisional Application Ser. No. 60/377,681, filed May 3, 2002.

1. TECHNICAL FIELD

This invention provides methods and materials related to viruses and the treatment of diseases such as cancer.

2. BACKGROUND INFORMATION

Measles virus (MV) causes the death of about a million children yearly, with fatality rates estimated to be approximately 5-10% in developing countries (*Measles Virus*, pp 13-33, ter Meulen and Billeter (ed.), Springer-Verlag, Berlin, 1995). Measles often is accompanied by immune suppression, which is thought to contribute to the susceptibility to secondary infections that account for most of the morbidity and mortality associated with the disease (Borrow and Oldstone (1995) *Curr. Top. Microbiol. Immunol.* 191:85-100). A live attenuated strain of the measles virus, MV-Edm, has been used to vaccinate against the disease and its sequelae (Duclos and Ward (1998) *Drug Saf.* 19:435-454). MV-Edm is not pathogenic. Vaccine recipients experience mild or no symptoms, and adverse consequences are extremely rare (*Measles Virus*, pp. 167-180, Fields, Knipe, et al. (ed.), Raven Press, Ltd., New York, 1995). Viruses such as MV have potential therapeutic use in treatment of human malignancies (see, e.g., PCT patent application Ser. No. PCT/US01/42259), but can result in immune suppression.

SUMMARY

The invention provides nucleic acids, polypeptides, and viruses containing nucleic acids and/or polypeptides. The invention also provides methods for using viruses to treat cancer patients. Specifically, the invention provides viral hemagglutinin (H) polypeptides, nucleic acid molecules encoding viral H polypeptides, and viruses containing H polypeptides and/or nucleic acids encoding H polypeptides. Such viruses are useful for treating cancer patients without causing immune suppression.

The nucleic acid molecules provided herein encode viral H polypeptides that are heterologous to naturally occurring H polypeptides (e.g., H polypeptides having the sequences set forth in SEQ ID NO:1, SEQ ID NO:2, or SEQ ID NO:3). Wild type viral H polypeptides can interact with cell surface receptors, including CD46 and signaling lymphocytic activating molecule, referred to herein as "SLAM". Nucleic acids of the invention have nucleotide sequences that are heterologous to naturally occurring viral H sequences, and thus can encode H polypeptides that contain amino acid sequence substitutions as compared to naturally occurring H polypeptides. As a result of these amino acid substitutions, H polypeptides of the invention can have less SLAM binding capability than naturally occurring H polypeptides. Nucleic acid molecules provided herein can be used to produce H polypeptides having reduced SLAM binding activity as compared to the activity of the corresponding, naturally occurring H polypeptides. The nucleic acid molecules also can be used to produce viruses that contain modified H polypeptides and have less SLAM-dependent cell entry than viruses containing the corresponding, naturally occurring H polypeptides.

As described herein, the invention also provides viruses containing a nucleic acid molecule encoding a modified H polypeptide. Typically, such viruses will express the modified H polypeptide and incorporate it into the virus particle. Because the modified viral H polypeptides of the invention have less SLAM binding ability than naturally occurring H polypeptides, viruses containing the modified H polypeptides have less SLAM-dependent cell entry than viruses containing the corresponding, naturally occurring H polypeptides. The reduction in SLAM-dependent cell entry can result in less immunosuppression when the virus infects or is administered to a subject. For example, the viruses described herein can be used to treat cancer patients without causing immune suppression.

The invention is based on the discovery that modified H polypeptides are incorporated into virus particles. The invention also is based on the discoveries that virus particles containing such modified H polypeptides retain the ability to infect $CD46^+$ cells and infected cells can produce new virus particles. In addition, the invention is based on the discovery that specific mutations in the MV H polypeptide partially or completely reduce SLAM-dependent entry of the virus into T cells and B cells, thus reducing immune suppression. Viruses containing the modified H polypeptides described herein are useful as therapeutic agents for the treatment of malignancies (e.g., ovarian cancer, breast cancer, and glioma), and because of their reduced SLAM-dependent cell entry, will not cause immunosuppressive activity that would result in treatment-related toxicity.

The invention features a polypeptide that contains an H polypeptide amino acid sequence, wherein mammalian $SLAM^+$ cells (e.g., CHO-SLAM cells or B95a cells) that contain the polypeptide and an F polypeptide consisting of the amino acid sequence set forth in SEQ ID NO:8 can fuse in a SLAM-dependent manner to a lesser extent than control mammalian $SLAM^+$ cells that contain a test H polypeptide consisting of the amino acid sequence set forth in SEQ ID NO:1 and the F polypeptide. The mammalian $SLAM^+$ cells may exhibit no SLAM-dependent fusion. The mammalian $SLAM^+$ cells can fuse in a CD46-dependent manner. A virus containing the polypeptide can have the ability to enter cells in a CD46-dependent manner.

The polypeptide also can contain a second amino acid sequence (e.g., a single chain antibody amino acid sequence or a growth factor amino acid sequence), wherein the second amino acid sequence is attached to the carboxy-terminal portion of the H polypeptide amino acid sequence.

Mammalian $CD46^+$ cells (e.g., Vero cells) that contain the polypeptide and the F polypeptide can fuse in a CD46-dependent manner to a lesser extent than control mammalian $CD46^+$ cells that contain a test H polypeptide and the F polypeptide. The mammalian $CD46^+$ cells may exhibit no CD46-dependent fusion.

The polypeptide can have an H polypeptide amino acid sequence that aligns with the amino acid sequence set forth in SEQ ID NO:1. The H polypeptide amino acid sequence can contain at least one amino acid selected from the group consisting of: (a) an amino acid other than phenylalanine at the position aligning with position 431 of the amino acid sequence; (b) an amino acid other than valine at the position aligning with position 451 of the amino acid sequence; (c) an amino acid other than tyrosine at the position aligning with position 481 of the amino acid sequence; and (d) an amino acid other than alanine at the position aligning with position 527 of the amino acid sequence. The H polypeptide amino acid sequence can contain at least two amino acids selected from the group, at least three amino acids selected from the group, or all four amino acids of the group.

The H polypeptide amino acid sequence can contain at least one amino acid selected from the group consisting of: (a) an amino acid other than tyrosine at the position aligning with position 529 of the amino acid sequence; (b) an amino acid other than aspartic acid at the position aligning with position 530 of the amino acid sequence; (c) an amino acid other than arginine at the position aligning with position 533 of the amino acid sequence; and (d) an amino acid other than tyrosine at the position aligning with position 553 of the amino acid sequence. The H polypeptide amino acid sequence can contain at least two amino acids selected from the group, at least three amino acids selected from the group, or all four amino acids of the group.

The invention also features a polypeptide that contains an H polypeptide amino acid sequence, wherein mammalian $CD46^+$ cells (e.g., Vero cells) containing the polypeptide and an F polypeptide consisting of the amino acid sequence set forth in SEQ ID NO:8 can fuse in a CD46-dependent manner to a lesser extent than control mammalian $CD46^+$ cells containing a test H polypeptide consisting of the amino acid sequence set forth in SEQ ID NO:1 and the F polypeptide. The mammalian $CD46^+$ cells may exhibit no CD46-dependent fusion. The mammalian $CD46^+$ cells can fuse in a SLAM-dependent manner. A virus containing the polypeptide can have the ability to enter cells in a SLAM-dependent manner.

The polypeptide can contain a second amino acid sequence (e.g., a single chain antibody amino acid sequence or a growth factor amino acid sequence), wherein the second amino acid sequence is attached to the carboxy-terminal portion of the H polypeptide amino acid sequence.

The polypeptide can have an H polypeptide amino acid sequence that aligns with the amino acid sequence set forth in SEQ ID NO:1. The H polypeptide amino acid sequence can contain at least one amino acid selected from the group consisting of: (a) an amino acid other than phenylalanine at the position aligning with position 431 of the amino acid sequence; (b) an amino acid other than valine at the position aligning with position 451 of the amino acid sequence; (c) an amino acid other than tyrosine at the position aligning with position 481 of the amino acid sequence; and (d) an amino acid other than alanine at the position aligning with position 527 of the amino acid sequence. The H polypeptide amino acid sequence can contain at least two amino acids selected from the group, at least three amino acids selected from the group, or all four amino acids of the group.

In another aspect, the invention features an isolated nucleic acid molecule that encodes the polypeptide of the invention. The invention also features an isolated nucleic acid molecule that encodes an F polypeptide and the polypeptide of the invention. The invention further features a vector containing the isolated nucleic acids of the invention. The vector can be, for example, an adenovirus vector, an adeno-associated virus vector, a herpes virus vector, a retrovirus vector, a lentivirus vector, a parvovirus vector, a Sindbis virus vector, an SV40 vector, or a molecular conjugate vector.

In another aspect, the invention features a cell (e.g., a CHO-SLAM cell, a B95a cell, or a Vero cell) containing the isolated nucleic acid molecule or the polypeptide of the invention. The cell can contain both the isolated nucleic acid molecule and the polypeptide of the invention.

In yet another aspect, the invention features a virus (e.g., a measles virus, a canine distemper virus, or a rinderpest virus) containing the isolated nucleic acid molecule or the polypeptide of the invention. The virus can contain both the nucleic acid molecule and the polypeptide of the invention.

The invention also features a method for inducing fusion between cells that contain an F polypeptide. The method can involve providing the cells with the polypeptide of the invention. The method can involve providing the cells with an F polypeptide and the polypeptide of the invention. The method can involve providing the cells with a nucleic acid molecule encoding the polypeptide of the invention, such that the cells contain the polypeptide. The method can involve providing the cells with an F polypeptide and a nucleic acid molecule encoding the polypeptide of the invention, such that the cells contain the polypeptide.

In another aspect, the invention features a method for reducing the number of viable tumor cells in a mammal (e.g., a human). The tumor cells can be ovarian tumor cells, breast tumor cells, prostate tumor cells, stomach tumor cells, colon tumor cells, rectal tumor cells, kidney tumor cells, lung tumor cells, brain tumor cells, glioma cells, lymphoma cells, melanoma cells, or myeloma cells. The method can involve administering to the mammal the vector of the invention. The method can involve administering to the mammal a dose of a virus (e.g., a measles virus, a canine distemper virus, or a rinderpest virus) effective to reduce the number of viable tumor cells, wherein the virus contains the polypeptide of the invention. The dose can have a virus titer greater than $10^8$ plaque forming units.

In another embodiment, the invention features a polypeptide containing an H polypeptide amino acid sequence that aligns with the amino acid sequence set forth in SEQ ID NO:1, where the H polypeptide amino acid sequence contains (a) an amino acid other than tyrosine at the position aligning with position 481 of the amino acid sequence and (b) an amino acid other than arginine at the position aligning with position 533 of the amino acid sequence. The H polypeptide amino acid sequence can contain (a) an alanine at the position aligning with position 481 of the amino acid sequence and (b) an alanine at the position aligning with position 533 of the amino acid sequence.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a column graph plotting the levels of soluble CD46-IgG and SLAM-IgG fusion polypeptides produced in transfected DF-1 cells. The polypeptides were detected by ELISA using the indicated antibodies.

FIG. 2 is a photograph of a western blot. Extracts from cells producing soluble, FLAG®-tagged H polypeptides were treated with or without DTT as indicated and subjected to SDS-PAGE. H polypeptides were detected by anti-FLAG® antibodies.

Figure 3:
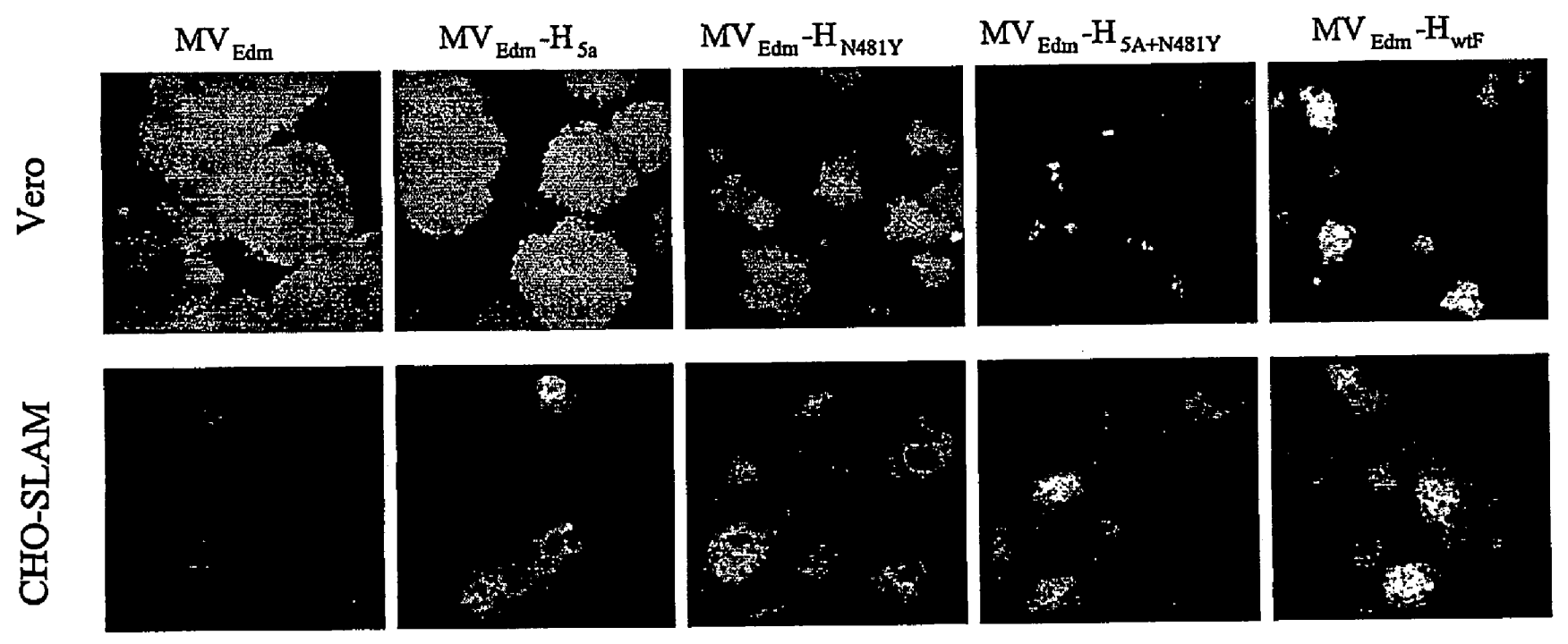

FIG. 3 is a series of fluorescence micrographs of Vero cells (CD46⁺) or CHO-SLAM cells (SLAM⁺) infected with the indicated recombinant viruses expressing green fluorescent protein (GFP) and different H polypeptides. Infection was detected by GFP fluorescence.

FIG. 4 is an amino acid sequence alignment of the MV and canine distemper virus (CDV) H polypeptide ectodomains (SEQ ID NO:4 and SEQ ID NO:5, respectively). Residues conserved between the two polypeptides are shown by dots in the CDV sequence. Mutations were generated at divergent residues and are indicated by underlining.

FIG. 5 is an amino acid sequence alignment of the MV, rinderpest virus (RV), and CDV H polypeptide ectodomains (SEQ ID NO:4, SEQ ID NO:6, and SEQ ID NO:7, respectively). Residues conserved between the three polypeptides are shown by dots in the RV and CDV sequences. Mutations were generated at conserved residues and are indicated by underlining.

FIG. 6A is a light micrograph of cells infected with the indicated viruses. Dark areas represent syncytia, indicating viral infection. FIG. 6B is a photograph of a western blot of extracts from Vero cells ($CD46^+$) and B95a cells ($SLAM^+$) infected with the indicated viruses. FIG. 6C is a fluorescent micrograph of Vero cells and B95a cells infected with recombinant MV expressing GFP and the indicated H polypeptides. Infection was detected by GFP fluorescence.

FIGS. 7A, 7B, and 7C are amino acid sequence listings for naturally occurring H polypeptides from the Edmonston MV strain, CDV, and RV, respectively.

FIG. 8 is the amino acid sequence of the naturally occurring F polypeptide from the Edmonston MV strain.

FIGS. 9A, 9B, and 9C are nucleic acid sequence listings that contain a sequence encoding the amino acid sequences set forth in SEQ ID NOs: 1, 2, and 3, respectively.

FIG. 10A is a schematic representation of a chimeric H polypeptide with the relative positions of mutations for ablation of CD46 or SLAM receptor binding identified. The single-chain antibody is displayed as a C-terminal extention of the H polypeptide. For H polypeptide detection by immunoblots, a Flag tag (DYKDDDDK; SEQ ID NO:12) was inserted into the start codon of the H polypeptide. The "Cyt. Tail" represents the cytoplasmic tail, while the "TM" represents the transmembrane domain. FIG. 10B is a schematic representation of the experiments using plasmids encoding the mutant H polypeptides and F polypeptide. Once co -transfected, the indicated receptor-positive cells were assessed for cell fusion.

FIG. 11 is a table presenting the syncytial counts and nuclei per syncytium observed in Vero cells ($CD46^+$ cells), CHO-SLAM cells ($SLAM^+$ cells), and CHO-CD38 cells ($CD38^+$ cells) transfected with the indicated nucleic acid. In the H polypeptide column, the "Edm" represents the wild-type H polypeptide having the sequence set forth in SEQ ID NO:1, the "CD38" represents a scFv against CD38, and the number-letter code (e.g., 481A) represents the point mutation made to the sequence set forth in SEQ ID NO:1. # The synsytia in 5 representative fields were counted, and the number of syncytia per well was calculated. The results represent means±SD. ↑↑↑ indicates that the cells were not countable since greater than 90% of the cells were in syncytia. * The average number of nuclei per syncytium was allocated a score of "–" (0 cells per syncytium), "±" (1-5 cells per syncytium), "+" (6-20 cells per syncytium), "++" (21-50 cells per syncytium), or "+++" (50>cells per syncytium).

FIG. 12A contains photographs of CHO-CD38 cells transfected with the indicated plasmids. FIG. 12B contains immunoblots demonstrating the levels of total or surface expression of the indicated H polypeptides in CHO-CD38 cells. FIG. 12C contains FACS analysis results demonstrating the intensity of fusion activity in CHO-CD38 cells transfected with a plasmid encoding the indicated H polypeptides.

FIG. 13A contains photographs of the indicated cells (top) transfected with plasmids encoding the indicated H polypeptides (side). FIG. 13B contains four bar graphs plotting the percent of cell viability for the indicated cells (top) transfected with plasmids encoding H polypeptides. Number 1 indicates Vero cells, number 2 indicates CHO-CD46 cells, number 3 indicates CHO-SLAM cells, number 4 indicates CHO-CD38 cells, number 5 indicates CHO-EGFR cells, and number 6 indicates MC38-CEA cells.

DETAILED DESCRIPTION

The invention provides nucleic acids, polypeptides, and viruses containing the nucleic acids and/or polypeptides. The invention also provides methods for using the viruses to treat cancer patients. Specifically, the invention provides nucleic acid molecules encoding viral hemagglutinin (H) polypeptides, viral H polypeptides, and viruses containing such nucleic acids and/or such H polypeptides. The viruses described herein can be used to treat cancer patients without causing immune suppression.

1. Nucleic Acids

The invention provides nucleic acid molecules that encode an H polypeptide that is (1) heterologous to any naturally occurring H polypeptide, and (2) has reduced SLAM binding as compared to a naturally occurring H polypeptide. The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acid molecules that are present in a viral genome, including nucleic acids that normally flank one or both sides of the nucleic acid in a viral genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Nucleic acids of the invention encode H polypeptides that are heterologous to any naturally occurring viral H polypeptide (i.e., are "modified" H polypeptides). The term "H polypeptide amino acid sequence" as used herein refers to any amino acid sequence that is at least 65 percent (e.g., at least 70, 75, 80, 85, 90, 95, 99, or 100 percent) identical to the sequence set forth in SEQ ID NO:1, SEQ ID NO:2, or SEQ ID NO:3.

The percent identity between a particular amino acid sequence and the amino acid sequence set forth in SEQ ID NO:1, SEQ ID NO:2, or SEQ ID NO:3 is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length H polypeptide amino acid sequence followed by multiplying the resulting value by 100. For example, an amino acid sequence that has 500 matches when aligned with the sequence set forth in SEQ ID NO:1 is 81.0 percent identical to the sequence set forth in SEQ ID NO:1 (i.e., 500÷617*100=81.0).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

A mutation in a nucleic acid molecule of the invention can be in any portion of the coding sequence that renders the encoded H polypeptide less able than the corresponding, naturally occurring H polypeptide to interact with a SLAM receptor. Nucleic acids of the invention typically contain nucleotide sequence variants at, for example, positions encoding amino acids involved in SLAM binding. Mutations at nucleotides encoding the amino acids at positions 529, 530, 533, and 553 (relative to SEQ ID NO:1, SEQ ID NO:2, or SEQ ID NO:3) are particularly useful. Nucleic acids of the invention also can include nucleotide sequence variants at positions encoding amino acids involved in CD46 binding. Mutations at nucleotides encoding the amino acids at positions 431, 451, 481, and 527 (relative to SEQ ID NO:1, SEQ ID NO:2, or SEQ ID NO:3) are particularly useful.

Nucleic acids encoding viral H polypeptides can be modified using common molecular cloning techniques (e.g., site-directed mutagenesis) to generate mutations at such positions. Possible mutations include, without limitation, substitutions (e.g., transitions and transversions), deletions, insertions, and combinations of substitutions, deletions, and insertions. Nucleic acid molecules can include a single nucleotide mutations or more than one mutation, or more than one type of mutation. Polymerase chain reaction (PCR) and nucleic acid hybridization techniques can be used to identify nucleic acids encoding H polypeptides having altered amino acid sequences.

Additional nucleic acid sequences can be included in a nucleic acid molecule of the invention. Such additional nucleic acid sequences include, without limitation, other viral sequences. For example, a nucleic acid molecule can contain a complete MV genomic sequence that includes, in a 5'-3' direction, the N, P, M, F, H, and L sequences, wherein the naturally occurring H sequence is replaced by a sequence encoding a modified H polypeptide that (1) has an amino acid sequence at least 65% identical to SEQ ID NO:1, SEQ ID NO:2, or SEQ ID NO:3 and (2) has less SLAM binding activity than a corresponding, naturally occurring H polypeptide. A nucleic acid molecule containing such viral nucleic acid sequences can be used to transfect cells (e.g., CHO cells) in order to produce infectious virus particles. Alternatively, a nucleic acid molecule can contain sequences that encode a modified H polypeptide and an F polypeptide (including, by way of example and not limitation, an F polypeptide having the amino acid sequence set forth in SEQ ID NO:8). Such a nucleic acid can contain an internal ribosome entry site (IRES) between the coding sequences.

The nucleic acid molecules provided herein also can contain nucleic acid sequences such that the nucleic acid molecules encode replication-competent virus (e.g., replication-competent MV). For example, a nucleic acid molecule of the invention can contain viral sequences such that replication-competent viruses expressing modified H polypeptides are produced. As described herein, such a nucleic acid molecule can be an MV cDNA vector containing a nucleic acid sequence encoding a modified H polypeptide.

Alternatively, the nucleic acid molecules provided herein can contain nucleotide sequences such that the nucleic acid molecules encode replication-defective virus (e.g., replication-defective MV). For example, a nucleic acid molecule of the invention can contain viral sequences such that replication-defective viruses expressing modified H polypeptides are produced.

Nucleic acids of the invention can encode polypeptides that contain an H polypeptide amino acid sequence coupled to a second amino acid sequence. The second amino acid sequence can be from a polypeptide that is a ligand for a cell surface receptor or that binds to another polypeptide on a cell surface. An amino acid sequence from a single chain antibody or from a growth factor is particularly useful. The second amino acid sequence can be at the amino-terminal end of the amino acid sequence of the H polypeptide extracellular domain, or at the carboxy-terminal end of the H polypeptide amino acid sequence. Location of a second amino acid sequence at the carboxy terminus of the H polypeptide is particular useful.

The invention also provides vectors containing nucleic acid that encodes an H polypeptide. Such vectors can be, without limitation, viral vectors, plasmids, phage, and cosmids. For example, vectors can be of viral origin (e.g., paramyxovirus vectors, SV40 vectors, molecular conjugate vectors, or vectors derived from adenovirus, adeno-associated virus, herpes virus, lentivirus, retrovirus, parvovirus, or Sindbis virus) or of non-viral origin (e.g., vectors from bacteria or yeast). A nucleic acid encoding an H polypeptide typically is inserted into a vector such that the H polypeptide is expressed. For example, a nucleic acid provided herein can be inserted into an expression vector. "Expression vectors" can contain one or more expression control sequences (e.g., a sequence that controls and regulates the transcription and/or translation of another sequence. Expression control sequences include, without limitation, promoter sequences, transcriptional enhancer elements, and any other nucleic acid elements required for RNA polymerase binding, initiation, or termination of transcription.

Nucleic acid molecules within the scope of the invention can be obtained using any method including, without limitation, common molecular cloning and chemical nucleic acid synthesis techniques. For example, PCR can be used to construct nucleic acid molecules that encode modified H polypeptides. PCR refers to a procedure or technique in which target nucleic acid is amplified in a manner similar to that described in U.S. Pat. No. 4,683,195, and subsequent modifications of the procedure described therein.

Nucleic acids of the invention can be incorporated into viruses by standard techniques. For example, recombinant techniques can be used to insert a nucleic acid molecule encoding a modified H polypeptide into an infective viral cDNA. Alternatively, a nucleic acid can be exogenous to a viral particle, e.g., an expression vector contained within a cell such that the polypeptide encoded by the nucleic acid is expressed by the cell and then incorporated into a new viral particle.

2. Polypeptides

As used here, a "polypeptide" refers to a chain of amino acid residues, regardless of post-translational modification (e.g., phosphorylation or glycosylation). Polypeptides of the invention are modified H polypeptides, and therefore are heterologous to naturally occurring H polypeptides. An H polypeptide of the invention has an H polypeptide amino acid sequence that is at least 65 percent (e.g., at least 70, 75, 80, 85, 90, 95, 99, or 100 percent) identical to the sequence set forth in SEQ ID NO:1, SEQ ID NO:2, or SEQ ID NO:3.

Naturally occurring H polypeptides typically have receptor-binding and hemagglutination activities, and functionally cooperate with viral F polypeptides to induce fusion between target cells. Such fusion can be mediated through interactions between H polypeptides and receptors on target cells (e.g., CD46 and SLAM).

H polypeptides of the invention can have less SLAM binding ability than a corresponding, naturally occurring H polypeptide. Cells that contain such an H polypeptide along with a naturally occurring F polypeptide (e.g., an F polypeptide having the amino acid sequence set forth in SEQ ID NO:8) can display less SLAM-dependent fusion than cells containing a naturally occurring H polypeptide that has the amino acid sequence of, for example, SEQ ID NO:1, SEQ ID NO:2, or SEQ ID NO:3. In addition, when such an H polypeptide is incorporated into a virus, the level of SLAM-dependent cell entry exhibited by the virus can be less than the level of SLAM-dependent cell entry exhibited by a wild type virus containing a corresponding, naturally occurring H polypeptide. For example, a measles virus containing an H polypeptide of the invention can have less SLAM-dependent entry into SLAM$^+$ cells than the amount of SLAM-dependent entry of a wild type MV-Edm into SLAM$^+$ cells. Cell entry via SLAM receptors can be assessed by standard techniques such as those described herein (see Examples 6 and 7).

H polypeptides of the invention that have reduced SLAM binding and confer reduced SLAM-dependent fusion and entry to cells and viruses, respectively, can retain the ability to bind to CD46. Cells containing such polypeptides therefore can fuse in a CD46-dependent manner, and viruses containing such polypeptides can exhibit CD46-dependent cell entry.

Alternatively, H polypeptides of the invention can have less CD46 binding ability than a corresponding, naturally occurring H polypeptide. Cells that contain such an H polypeptide along with a naturally occurring F polypeptide (e.g., an F polypeptide having the amino acid sequence set forth in SEQ ID NO:8) can display less CD46-dependent fusion than cells containing a naturally occurring H polypeptide that has the amino acid sequence of, for example, SEQ ID NO:1, SEQ ID NO:2, or SEQ ID NO:3. In addition, when such an H polypeptide is incorporated into a virus, the level of CD46-dependent cell entry exhibited by the virus can be less than the level of CD46-dependent cell entry exhibited by a wild type virus containing a corresponding, naturally occurring H polypeptide. For example, a measles virus containing an H polypeptide of the invention can have less CD46-dependent entry into CD46$^+$ cells than the amount of CD46-dependent entry of a wild type MV-Edm into CD46$^+$ cells. Cell entry via CD46 receptors can be assessed by standard techniques such as those described herein (see Examples 6 and 7).

H polypeptides of the invention that have reduced CD46 binding and confer reduced CD46-dependent fusion and entry to cells and viruses, respectively, can retain the ability to bind to SLAM. Cells containing such polypeptides therefore can fuse in a SLAM-dependent manner, and viruses containing such polypeptides can exhibit SLAM-dependent cell entry.

H polypeptides of the invention typically contain at least one amino acid substitution relative to the corresponding wild type H polypeptides (e.g., $H_{wtF}$ or $H_{Edm}$, the naturally occurring H polypeptides from the wild type F and MV-Edm strains, respectively). Such amino acid substitutions typically are located at positions involved in the binding of H polypeptides to SLAM receptors. Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine.

Non-conservative amino acid substitutions may replace an amino acid of one class with an amino acid of a different class. Non-conservative substitutions can make a substantial change in the charge or hydrophobicity of the gene product. Non-conservative amino acid substitutions also can make a substantial change in the bulk of the residue side chain, e.g., substituting an alanine residue for an isoleucine residue. Examples of non-conservative substitutions include the substitution of a basic amino acid for a non-polar amino acid or a polar amino acid for an acidic amino acid.

Amino acid substitutions that are particularly useful can be found at, for example, one or more positions corresponding to amino acids 529, 530, 533, and 553 of a full-length H polypeptide having the amino acid sequence set forth in SEQ ID NO: 1, SEQ ID NO:2, or SEQ ID NO:3. Such substitutions (1) render the H polypeptide less able than a naturally occurring H polypeptide to bind to SLAM, (2) confer less SLAM-dependent fusion between cells than would a naturally occurring H polypeptide, and (3) confer less SLAM-dependent cell entry to a virus than would a naturally occurring H polypeptide.

Other amino acid substitutions that are particularly useful can be found at, for example, one or more positions corresponding to amino acids 431, 451, 481, and 527 of a full-length H polypeptide having the amino acid sequence set forth in SEQ ID NO:1, SEQ ID NO:2, or SEQ ID NO:3. Such substitutions (1) render the H polypeptide less able than a naturally occurring H polypeptide to bind to CD46, (2) confer less CD46-dependent fusion between cells than would a naturally occurring H polypeptide, and (3) confer less CD46-dependent cell entry to a virus than would a naturally occurring H polypeptide.

H polypeptides provided herein also can contain substitutions from both of the groups defined above. Such H polypeptides typically exhibit less SLAM binding and less CD46 binding than a naturally occurring H polypeptide. Cells containing such an H polypeptide can display less SLAM-dependent fusion and less CD46-dependent fusion than cells containing a naturally occurring H polypeptide. Furthermore, a virus containing such an H polypeptide can exhibit less SLAM-dependent cell entry and less CD46-dependent cell entry than a virus containing a naturally occurring H polypeptide.

An H polypeptide amino acid sequence of the invention can be coupled to a second amino acid sequence. Such coupling can occur through, for example, peptide bonding. As used herein, a "second amino acid sequence" is an amino acid sequence that is exogenous to an H polypeptide amino acid sequence. Typically, second amino acid sequences that are particularly useful can bind to cell surface receptors other than SLAM and CD46. Such second amino acid sequences therefore can serve to target an H polypeptide of the invention to a particular type of cell (e.g., a tumor cell), depending on the receptor targeted by the second amino acid sequence. Second amino acid sequences from growth factors and single chain antibodies are particularly useful. A second amino acid sequence can be at the amino-terminal end of the amino acid sequence of the H polypeptide extracellular domain, or at the carboxy-terminal end of the H polypeptide amino acid sequence. Localization of a second amino acid sequence at the carboxy terminus of an H polypeptide amino acid sequence is particularly useful.

An H polypeptide that is incorporated into a virus can be encoded by a nucleic acid molecule that is present within the virus. Alternatively, a virus can take up an exogenous H polypeptide that is expressed by, for example, a cell. Amino acid substitutions within viral H polypeptides of the invention can result in viruses having, for example, less binding to SLAM receptors and less SLAM-dependent cell entry than the levels of SLAM binding and SLAM-dependent cell entry exhibited by viruses containing naturally occurring H polypeptides. Levels of binding to SLAM receptors and SLAM-dependent cell entry can be measured by techniques such as, for example, those described herein (see Examples 5, 6, and 7).

H polypeptides can be produced using any method. For example, H polypeptides can be obtained by extraction from viruses, isolated cells, tissues and bodily fluids. H polypeptides also can be produced by chemical synthesis. Alternatively, H polypeptides of the invention can be produced by standard recombinant technology using heterologous expression vectors encoding H polypeptides. Expression vectors can be introduced into host cells (e.g., by transformation or transfection) for expression of the encoded polypeptide, which then can be purified. Expression systems that can be used for small or large scale production of H polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules of the invention, and yeast (e.g., *S. cerevisiae*) transformed with recombinant yeast expression vectors containing the nucleic acid molecules of the invention. Useful expression systems also include insect cell systems infected with recombinant virus expression vectors (e.g., baculovirus) containing the nucleic acid molecules of the invention, and plant cell systems infected with recombinant virus expression vectors (e.g., tobacco mosaic virus) or transformed with recombinant plasmid expression vectors (e.g., Ti plasmid) containing the nucleic acid molecules of the invention. H polypeptides also can be produced using mammalian expression systems, which include cells (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

3. Viruses

The invention provides viruses containing the nucleic acid molecules and/or polypeptides described herein. For example, the invention provides recombinant viruses that encode polypeptides (e.g., modified H polypeptides) that are heterologous to a corresponding, naturally occurring H polypeptide.

Viruses containing the nucleic acid molecules described herein are not required to express the encoded polypeptide. For example, a virus (e.g., an Adenovirus) can be engineered to contain a nucleic acid that encodes an H polypeptide of the invention. In this case, the engineered virus may or may not express the encoded H polypeptide. Viruses containing nucleic acid that encodes an H polypeptide can be used to deliver the nucleic acid to cells, such that the cells express the encoded H polypeptide.

Alternatively, viruses that contain a nucleic acid molecule described herein can express the encoded H polypeptide. For example, an MV containing a nucleic acid molecule that encodes a modified H polypeptide can display the modified H polypeptide on its surface. Such a virus can target cells for viral entry.

Any virus can contain a nucleic acid molecule encoding a modified viral H polypeptide of the invention. Viruses can be RNA viruses or DNA viruses. Viruses can be, for example, nonsegmented negative strand RNA viruses belonging to the Mononegavirales group (e.g., MV, human parainfluenzavirus, rabies virus, respiratory syncytial virus, and mumps virus). Viruses also can be influenza viruses, which have a segmented RNA genome of negative polarity and share several structural features with MV. Viruses also can be, without limitation, enveloped viruses such as herpes simplex virus, and retroviruses such as murine leukemia virus and human immunodeficiency virus.

Viruses of the invention can be attenuated. As used herein, the term "attenuated" refers to a virus that is immunologically related to a wild type virus but which is not itself pathogenic. An attenuated MV, for example, does not produce classical measles disease. Attenuated viruses typically are replication-competent, in that they are capable of infecting and replicating in a host cell without additional viral functions supplied by, for example, a helper virus or a plasmid expression construct encoding such additional functions.

Viruses containing a nucleic acid molecule that encodes a modified H polypeptide having reduced SLAM binding activity can be replication-competent or replication-defective. In addition, the nucleic acid molecule within the virus can contain any of the nucleic acid sequences described herein. For example, a measles virus can contain a complete MV genome that has a nucleotide sequence encoding a heterologous H polypeptide. Such a virus can display less SLAM-dependent cell entry than a wild type virus containing the corresponding, naturally occurring H polypeptide. The level of SLAM-dependent cell entry can be assessed by standard techniques such as, for example, those described herein.

Any method can be used to identify viruses containing a nucleic acid molecule of the invention. Such methods include, without limitation, PCR and nucleic acid hybridization techniques such as Northern and Southern analysis. In some cases, immunohistochemistry and biochemical techniques can be used to determine if a virus contains a particular nucleic acid molecule by detecting the expression of a polypeptide encoded by that particular nucleic acid molecule (see, e.g., Example 7).

4. Methods of Using H Polypeptides, Nucleic Acids, and Viruses of the Invention

H polypeptides and/or nucleic acids of the invention can be administered to cells in order to induce cell fusion. For example, a nucleic acid molecule (e.g., a viral vector) encoding a modified H polypeptide as well as any other polypeptide (e.g., an F polypeptide) can be administered to a tumor in order to induce fusion between tumor cells, ultimately resulting in cell death.

Viruses that contain nucleic acids and/or polypeptides provided herein also can be administered to cells (e.g., in vivo or in vitro) to induce cell fusion. Incorporation of the encoded H polypeptide into the virus is not required. For example, a virus (e.g., an Adenovirus) can be engineered to contain a nucleic acid encoding an H polypeptide that is not incorporated into the virus. Such a virus can be administered to a cell population in order to deliver the nucleic acid encoding the H polypeptide into the cells. The infected cells then can express the encoded H polypeptide, leading to cell fusion. Viruses provided herein that contain nucleic acids encoding H polypeptides and contain the H polypeptides also are useful for inducing cell fusion. An MV, for example, that contains a nucleic acid encoding an H polypeptide also can contain the encoded H polypeptide. Such a virus can be used to target particular cells as described herein. The H polypeptide then can be expressed within the targeted cells, inducing the cells to fuse. It is noted that an F polypeptide can be used with the H polypeptides described herein. For example, a single virus can contain nucleic acid that encodes both an H polypeptide and an F polypeptide.

Viruses provided herein can be used to treat cancer patients. A particular virus can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). A virus can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., Vero cells) in culture. After 2 to 3 hours of viral adsorption, the inoculum is removed, and cells are overlaid with a mixture of cell culture medium and agarose or methylcellulose (e.g., 2 ml DMEM containing 5% FCS and 1% SeaPlaque agarose). After about 3 to about 5 days, cultures are fixed with 1 ml of 10% trifluoroacetic acid for about 1 hour, then UV cross-linked for 30 minutes. After removal of the agarose overlay, cell monolayers are stained with crystal violet and plaques are counted to determine viral titer. Virus is harvested from cell syncytia by scraping cells from the dishes, subjecting them to freeze/thawing (e.g., approximately two rounds), and centrifuging. The cleared supernatants represent "plaque purified" virus.

Viral stocks can be produced by infection of cell monolayers (e.g., adsorption for about 1.5 hours at 37° C.), followed by scraping of infected cells into a suitable medium (e.g., Opti-MEM; Gibco/Invitrogen, Carlsbad, Calif.) and freeze/thaw lysis. Viral stocks can be aliquoted and frozen, and can be stored at −70° C. to −80° C. at concentrations higher than the therapeutically effective dose. A viral stock can be stored in a stabilizing solution. Stabilizing solutions are known in the art and include, without limitation, sugars (e.g., trehalose, dextrose, glucose), amino acids, glycerol, gelatin, monosodium glutamate, $Ca^{2+}$, and $Mg^{2+}$.

Methods of the invention are useful for treating cancer (i.e., reducing tumor size, inhibiting tumor growth, or reducing the number of viable tumor cells). As used herein, "reducing the number of viable tumor cells" is meant to encompass (1) slowing the rate of growth of a population of tumor cells such that after a certain period of time, a tumor in a treated individual is smaller than it would have been without treatment; (2) inhibiting the growth of a population of tumor cells completely, such that a tumor stops growing altogether after treatment; and/or (3) reducing the population of tumor cells such that a tumor becomes smaller or even disappears after treatment.

Viruses provided herein can be administered to a cancer patient by, for example, direct injection into a group of cancer cells (e.g., a tumor) or intravenous delivery to cancer cells. Types of cancer cells susceptible to treatment with viruses include neuronal cells, glial cells, myelomonocytic cells, and the like. Methods of the invention can be used to treat types of cancer that include, but are not limited to, myeloma, melanoma, glioma, lymphoma, and cancers of the lung, brain, stomach, colon, rectum, kidney, prostate, ovary, and breast. An attenuated measles virus containing a modified H polypeptide can be used to treat, for example, a lymphoma (e.g., Non-Hodgkin's Lymphoma).

Viruses containing polypeptides that have H polypeptide amino acid sequences coupled to a second amino acid sequence can be particularly useful for treating cancer or reducing tumor growth. For example, a virus containing an H polypeptide coupled to a growth factor amino acid sequence can target cells (e.g., tumor cells) that have growth factor receptors on their surface.

Viruses of the invention can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe as a vaccine (e.g., $10^3$ pfa) and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

Viruses provided herein can be delivered in a dose ranging from, for example, about $10^3$ pfu to about $10^{12}$ pfu (typically $>10^8$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same or a different modified virus) can be administered by the same route as initially used or by another route. A therapeutically effective dose can be delivered in several discrete doses (e.g., days or weeks apart) and in one embodiment of the invention, one to about twelve doses are provided. Alternatively, a therapeutically effective dose of attenuated measles virus can be delivered by a sustained release formulation.

Viruses provided herein can be administered using a device for providing sustained release. A formulation for sustained release of a virus can include, for example, a polymeric excipient (e.g., a swellable or non-swellable gel, or collagen). A therapeutically effective dose of a virus can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. Alternatively, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

Viruses of the invention can be directly administered. For example, a virus can be injected directly into a tumor (e.g., a lymphoma) that is palpable through the skin. Ultrasound guidance also can be used in such a method. Alternatively, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of a virus also can be directly administered to a group of cancer cells that is visible in an exposed surgical field.

Viruses provided herein also can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of virus therapy can be monitored by evaluating changes in clinical symptoms (known in the art for each particular type of cancer) or by direct monitoring of the size of a group of cancer cells or tumor. A method for using a virus of the invention to treat cancer is considered effective if the cancer cell number, tumor size, tumor specific antigen level, and/or other clinical symptoms are reduced by at least 10 percent following administration of virus. For a solid tumor, for example, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

The invention will be further described in the following examples, which do not limit the scope of the invention described in the claims.

EXAMPLES

Example 1

Production of Soluble Receptor Polypeptides

Soluble versions of the receptors CD46 and SLAM were produced to facilitate a quantitative comparison of binding efficiencies. Both soluble receptors were produced as fusion polypeptides with immunoglobulin (Ig) G heavy chains to yield dimeric molecules with readily accessible tags for purification and detection purposes.

Soluble CD46 contains a simple deletion of the transmembrane and cytoplasmic domains of the molecule, leaving 303 amino acids encompassing the four CCP domains and a serine-threonine-proline rich region fused to the mouse IgG heavy chain (sCD46-mIgG). Soluble SLAM fused to the rabbit IgG domain (sSLAM-rIgG) is based on a naturally occurring, alternatively spliced form of human SLAM in which the 30 amino acids encompassing the entire transmembrane region (Cocks et al. (1995) *Nature* 376:260-263) are deleted. As a result, this form of SLAM is secreted, and its cytoplasmic tail becomes a part of the ectodomain. The reciprocal fusion polypeptides (sCD46-rIgG and sSLAM-mIgG) also are produced for use as matched controls in binding experiments.

sCD46-mIgG and sSLAM-rIgG were expressed from RCASBP(A), a replication competent retroviral vector derived from avian leukosis virus (ALV; see *Methods in Cell Biology*, Emerson and Sweeney, eds., pp. 179-214, 1998). Nucleic acids encoding the soluble receptor-IgG fusion polypeptides were subcloned into the RCASBP(A) vector as replacements of the non-essential src gene of ALV. Sequencing confirmed the correct location and authenticity of the inserted nucleic acids.

RCASBP(A)-sCD46-mIgG and RCASBP(A)-sSLAM-rIgG were transfected into the ALV-permissive DF-1 cell line (a permanent, non-transformed cell line derived from chicken embryo fibroblasts). The transfections yielded replicating recombinant ALV, as demonstrated by increasing levels of ALV p27 protein in the extracellular medium of DF-1 cells over time. An ELISA method was used to measure the levels of the soluble receptors in the extracellular medium. By this method, the IgG heavy chain of each fusion polypeptide was captured onto a solid phase by an anti-species antibody (i.e., anti-mouse IgG for sCD46-mIgG and anti-rabbit IgG for sSLAM-rIgG). Following incubation with clarified supernatant from transfected DF-1 cells, the IgG part of each fusion polypeptide was detected with an anti-species antibody coupled to horse radish peroxidase (HRP). The presence of the receptors was confirmed by detecting the polypeptides using either a rabbit anti-CD46 antibody visualized with anti-rabbit HRP, or a mouse anti-SLAM antibody visualized with anti-mouse HRP. As shown in FIG. 1, the receptor and IgG portions of both polypeptides were detected.

To assess whether the soluble receptor-IgG polypeptides were of the expected size, polypeptides were precipitated from clarified supernatants of transfected DF-1 cells using protein G-coupled agarose and then subjected to Western analysis. As with the ELISA assay, the IgG portions of the fusion polypeptides were detected using anti-species antibodies conjugated to HRP, and receptors were visualized using anti-CD46 or anti-SLAM antibodies. Western blotting revealed a sCD46-mIgG polypeptide of about 100 kD and a slightly smaller sSLAM-rIgG polypeptide. This was consistent with the predicted molecular weights of the two fusion polypeptides, further confirming correct expression.

Production of μg amounts of these polypeptides was achieved by increasing the incubation temperature to 39° C. and collecting 10 ml supernatant every other day for about 10 passages. Each aliquot contained 30-50 ng/ml of the sCD46-mIgG and sSLAM-rIgG polypeptides.

Alternatively, concentrated preparations of soluble SLAM and CD46 are obtained by taking advantage of the IgG tags fused to each receptor molecule. Large volumes of supernatants from transfected DF-1 cells are passed over a protein G column (Pierce, Rockford, Ill.) and bound receptor-IgG fusion polypeptides then are eluted. Stable cell lines are generated to produce larger amounts of the soluble receptor polypeptides. Toward that end, the coding regions of sCD46-mIgG and sSLAM-rIgG have been subcloned into the expression vector TFAneo (*Methods in Cell Biology*, supra), which carries a neomycin resistance gene. Transfection of these plasmids into a chosen cell-line and subsequent selection in G418-containing medium allows the generation of cell lines stably producing the soluble receptor-IgG fusion polypeptides.

Example 2

Production of Soluble H Polypeptides

Soluble forms of H polypeptides were produced to facilitate quantitative comparison of receptor binding efficiencies. For detection purposes, an epitope tag was added to the transmembrane-proximal amino-terminus of the ectodomain of CDV H. Regions encoding the endogenous signal peptide and the transmembrane segment (up to position 59) were substituted by the coding region of a FLAG® epitope. The modified coding region was synthesized by overlap extension PCR and joined in frame to the coding region for the signal peptide of the murine Ig kappa chain in plasmid pSecTag2a (Invitrogen, Carlsbad, Calif.), for expression under the control of a strong constitutive CMV promoter.

Murine myeloma cells P3X63-Ag8.653; American Type Culture Collection, Manassas, Va.) were used to generate cell lines stably expressing soluble CDV H polypeptides. To screen clones for high expression levels, cells were incubated with serum free medium for 24 hours, and 200 μl of the culture supernatants were overlaid on ELISA plates. The presence of soluble H polypeptide was assessed using an anti-FLAG® antibody, and clones with high expression levels were selected for further experiments. Western blot analysis under reducing (+DTT) and non-reducing (−DTT) conditions revealed that the size of the soluble H polypeptide was similar to the membrane bound form, and that its ability to dimerize was maintained, suggesting that the soluble polypeptide was correctly folded. Preliminary quantitation experiments indicated that the concentration of polypeptide in the supernatant was as high as 100 ng/ml.

Figure 2:
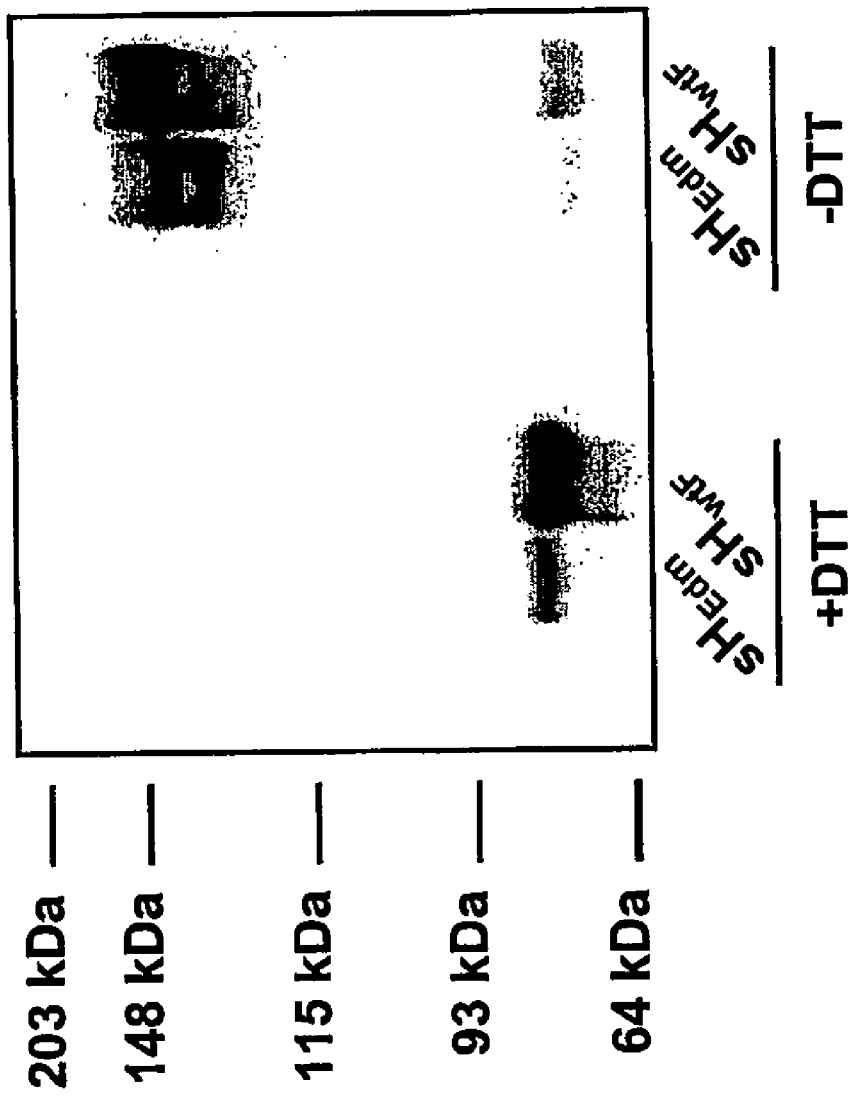

FLAG®-tagged soluble forms of the H polypeptides from the attenuated MV strain Edmonston ($sH_{Edm}$) and the wild type strain F ($sH_{wtF}$) were subsequently produced. The coding regions of the $H_{Edm}$ and $H_{wtF}$ sequences were inserted in the expression vector pCG, and the expression vectors were used to transfect CHO cells. Western blotting revealed that $sH_{Edm}$ and $sH_{wtF}$ were secreted from these cells: 5 μl of cell supernatants were reduced with DTT, separated by PAGE, and examined using anti-FLAG® antibodies. A strong signal at the expected molecular weight was detected in lanes $sH_{Edm}$/+DTT and $sH_{wtF}$/+DTT (FIG. 2). When the same supernatants were evaluated without a reducing agent, the apparent molecular weight of the material approximately doubled, consistent with dimerization. For binding assays, these polypeptides are purified in μg amounts using a centrifugal filter devices such as the Amicon Centriplus filter (Millipore, Bedford, Mass.). Alternatively, an anti-FLAG® M1 agarose column (catalog #A1080, Sigma, St. Louis, Mo.) is used for purification. Soluble H polypeptides containing amino acid substitutions are produced in the same manner.

Example 3

Production of Stable Cell Lines Expressing Equivalent Amounts of CD46 or SLAM

To assess the binding characteristics of viral particles and soluble H polypeptides to membrane-bound receptors, CHO cells expressing different CD46 variants have been produced (Buchholz et al. (1996) *J. Virol.* 70:3716-3723; Devaux et al. (1997) *J. Virol.* 71:4157-4160). CHO-SLAM cells also are available (Tatsuo et al. (2000) *Nature* 406:893-897). Using these cell lines, the relative binding efficiency of different viruses is measured based on known quantities of MV infectious particles or H polypeptides. Without quantitative data of the relative amounts of SLAM or CD46 polypeptides at the cell surface, however, the strength of binding to the two receptors cannot be compared.

To directly compare the quantity of SLAM or CD46 expressed on the cell surface, the receptors are tagged on their cytoplasmic tails with a FLAG® tag epitope, and cell lines stably expressing different levels of these polypeptides are obtained after G418 selection of CHO cells. Transfectants expressing different amounts of SLAM or CD46 are chosen from clones that arise from single cells sorted with monoclonals MCI 20.6 (CD46) or IPO-3 (SLAM). Cell surface polypeptides then are biotinylated and quantitatively detected by Western blots based on the FLAG® tag. Through such an analysis, pairs of cell lines that express similar amounts of the receptor polypeptides on their surfaces are identified.

Example 4

Recovery of Viruses Differing Only in their H Polypeptides

Several recombinant viruses differing only in the amino acid sequences of their H polypeptides were produced. To facilitate detection of the recombinant viruses, a GFP reporter gene was inserted into the MV-Edm genome (p(+)MVgreen). The H gene of p(+)MVgreen then was replaced by genes encoding four other H polypeptides: (1) the H polypeptide of the wtF clinical strain ($H_{wtF}$), (2) an $H_{Edm}$ polypeptide having a mutation to asparagine at position 481, (3) a mutant with alanines substituted at positions 473-477 (Patterson et al. (1999) *Virology* 256:142-151), and (4) an H polypeptide containing a mutation to asparagine at position 481 and alanines substituted at positions 473-477. The resulting plasmids were used for recovery of infectious viruses. Recombinant viruses with all four mutant H polypeptides, as well as MV-Edm$_{green}$ were recovered using a method based on a helper cell line (Radecke et al. (1995) *EMBO J.* 14:5773-5784). The "rescue" cell line 293-3-46 was overlaid with B95-8 cells to isolate the mutants with asparagine 481. These recombinants then were propagated in B95-8 cells. A similar experimental protocol is used to recover other MV recombinants.

Virus particles are purified using a protocol based on clarification of cell supernatants and concentration on a 60% sucrose cushion (Cathomen et al. (1998) *EMBO J.* 17:3899-3908; Schneider et al. (2000) *J. Virol.* 74:9928-9936). MV titers in supernatants typically do not exceed $10^6$/ml, setting a low initial level for purification protocols. Nevertheless, virus particles produced by this method have been purified in sufficient amounts to determine their relative binding strengths to CD46 (Buchholz et al. (1997) *J. Biol. Chem.* 272:22072-22079).

Example 5

Binding Assays

FACS-based binding assays. Soluble forms of the CD46 and SLAM receptors consisting of the receptor ectodomains fused to an immunoglobulin constant region were generated as described above. In vitro binding assays based on FACS analysis are performed using these soluble polypeptides. Cells either transiently expressing mutant H polypeptides or infected with the corresponding viruses are incubated with soluble receptors, and the binding is detected by FACS analysis using anti-mouse or anti-rabbit FITC-coupled antibodies. The level of H polypeptide at the cell surface is assessed in parallel using antibodies specific for the extracellular domain. A dilution series of the soluble receptor enables a quantitative estimate of receptor binding and permits comparison between polypeptides.

The FACS based assay is used to assess the ability of H polypeptides at the cell surface to bind soluble receptor. It is conceivable, however, that H polypeptides are held in a different conformation at the cell surface than in a viral particle, which may affect their receptor binding abilities. It therefore also is useful to measure the binding of purified virus particles to cells expressing CD46 and SLAM by a method such as that previously used to measure binding of MV-Edm to CD46 mutants (Buchholz et al. (1997) supra). In this method, viral particles are incubated with cells expressing either CD46 or SLAM on their surface (e.g., CHO-CD46 and CHO-SLAM, or the cell lines described above). Bound virus is detected using antibodies against the H polypeptide ectodomain followed by an anti-species FITC conjugate.

Biosensor assays. A soluble form of the MV H polypeptide and stable CHO cell lines expressing variants of the CD46 receptor have been used to study binding, revealing an avidity of 5.2±1.9 nM (Devaux et al. supra). Such an assay typically is not appropriate for measuring subtle differences in binding, however. Biosensor methods (e.g., surface plasmon resonance) are more useful for precisely measuring binding affinities of MV H polypeptides for soluble receptor-IgG molecules. In these assays, protein G (1-5 µg) is immobilized on BIAcore CM5 sensor chips via native amine groups. Similar amounts of the sCD46-mIgG and sSLAM-rIgG polypeptides then are bound to the protein G support by affinity capture. Increasing amounts of purified sH polypeptides (in the high ng to µg range) are used for the determination of binding efficiency with a Biacore 3000 system (Biacore AB, Piscataway, N.J.). Affinity constants are determined using separate $k_{on}$ and $k_{off}$ nonlinear regression with BIA evaluation software. This method also is used to examine the attachment of purified recombinant MV particles incorporating different H polypeptides to the biosensor surface and to measure the binding of soluble forms of the receptors to these particles.

Quantitative cell fusion assay. Visual screening of fusion on cell monolayers is sufficient for an initial, broad categorization of the fusion-support capacity of the H polypeptide mutants, but quantitative measurements of fusion-support activity can be performed. The assay of Nussbaum et al. ((1995) *J. Virol.* 69:3341-3349) is useful for this purpose. Cells are seeded at about 70% confluence in 24-well plates the day prior to transfection. For each construct, one well is transfected with expression plasmids encoding the H polypeptide (0.8 µg) and the F polypeptide (0.2 µg), along with a reporter plasmid (0.3 µg) containing the luciferase gene under control of a T7 promoter followed by an EMCV IRES to ensure translation. An additional well corresponding to each transfected well is infected with a host range mutant of vaccinia virus Ankara that expresses the T7 polymerase (Sutter et al. (1995) *FEBS Lett.* 371:9-12) with a MOI of 0.1. Six hours after transfection or infection, respectively, the cells are washed three times with PBS, trypsinized, and resuspended in 1 ml DMEM with 10% fetal calf serum. Cells from one transfected and one infected well each are mixed and seeded into two new wells. Twenty-four to 48 hours after transfection cells are lysed, and both wells are assayed for luciferase expression.

Example 6

Entry of Recombinant MV through Different Receptors, and their Dissemination in Human PBMC The efficiency with which the five recombinant viruses (described in Example 4) entered cells through different receptors was then examined by detecting GFP in infected Vero cells (expressing only CD46) and CHO-SLAM cells (FIG. 3). The most striking observation was that all viruses entered both cell lines, negating exclusive entry through one or the other receptor. Nevertheless, MVEdm-$H_{wtF}$ entered best in CHO-SLAM cells, MV-Edm best in Vero cells, and the other viruses had intermediate levels of entry, as monitored indirectly by GFP production. Analysis of polypeptide levels by Western blotting confirmed these observations.

Taking advantage of the fact that cells productively infected with these recombinant MVs emitted green light upon activation, the infection of MVEdm$_{green}$, MVEdm$_{green}$-H$_{N481}$, and MVEdm$_{green}$-H$_{wtF}$ was monitored in monocytes and T-lymphocytes. Human peripheral blood mononuclear cells (PBMC) were isolated from whole blood by low speed centrifugation on a Ficoll-paque layer. PBMC were purified into monocyte (M) or lymphocyte (L) populations by magnetic separation. The separated cells were stimulated by treatment with either granulocyte macrophage-colony stimulating factor (GM-CSF; M fraction) or a mixture of GM-CSF and phytohemagglutinin (L fraction), infected at a MOI of 0.1, and cultured for three days. CD4 and CD8 cells in the L fraction then were analyzed separately for GFP expression, whereas the complete M fraction was subjected to the same procedure. Cells were harvested 1, 3, and 5 days post-infection and assayed by FACS analysis for expression of GFP. Infection of different sub-populations is evaluated by preincubation of infected PBMC with phycoerythrin-conjugated mouse anti-human CD14, CD4, and CD8 antibodies and analysis by two-color FACS.

These experiments revealed that MVEdm-H$_{wtF}$ infected T cells more efficiently than MVEdm (Table 1). MVEdm-H$_{wtF}$ also efficiently infected monocytes. Expression of the two MV receptors in these cell populations then was assessed. SLAM expression was detected in most CD14 positive cells (monocyte fraction) not only one day after stimulation with GM-CSF, but also immediately after collection. These results confirmed the high sensitivity of the assay.

TABLE 1

Percentage of cells expressing GFP after infection with different viruses

|  | MVEdm | MVEdm-H$_{wtF}$ |
|---|---|---|
| L fraction |  |  |
| CD4 | 5.0 | 18.0 |
| CD8 | 5.3 | 13.9 |
| M fraction | 0.9 | 7.0 |

Example 7

Construction and Characterization of a Collection of H Polypeptide Mutants

H polypeptide residues important for virus attachment to CD46 and SLAM were identified in order to facilitate the production of viruses with tight receptor specificity. Mutagenesis was restricted to amino acids 382-582. The first round of mutagenesis excluded amino acids conserved between MV and CDV, another morbillivirus that does not interact with CD46. The homology criterion was important to retain conserved backbone residues, the modification of which may impair polypeptide folding. In addition, all cysteines in the selected region were preserved.

As shown in FIG. 4, approximately 90% of the remaining 115 amino acids were mutagenized in blocks of 2-4 residues, for a total of 45 mutants. Charged and polar residues were substituted with alanine, while serine was used to replace apolar residues. These small amino acids were used to limit structural interference that might lead to reduced polypeptide folding and transport. After mutagenesis, the sequences were confirmed and the polypeptides were expressed in Vero cells for western blotting to is verify that they had the expected size.

The function of all clones was examined in a fusion-support test based on the complementation of the standard F polypeptide for its ability to fuse cells (as described in Example 5). Clones expressing H$_{wtF}$ and H$_{Edm}$ also were tested. These tests were performed in cells expressing CD46 but not SLAM (Vero cells) or the opposite combination of MV receptors (CHO-SLAM cells). Of 45 mutants tested, 41 were found to have similar fusion-support function in both cell lines (26 had intermediate or strong fusion-support function, and 15 minimal or no fusion-support function), while 4 had a pronounced differential function (Table 2; Y481N, 430-431, 451-452, and 552-553). These results demonstrate that the CD46-dependent fusion and SLAM-dependent fusion activities of an H polypeptide can be separated. The mutants also were assayed to verify that the polypeptides were correctly folded and reached the cell surface.

TABLE 2

CD46- and SLAM-dependent fusion

|  | Vero | CHO-SLAM |
|---|---|---|
| H$_{Edm}$ | + + + + | + + + + |
| H$_{wtF}$ | + | + + + + |
| Y481N | + | + + + + |
| 430-431 | + | + + + + |
| 451-452 | + | + + + |
| 527-528 | 0 | + + + |
| 529-530 | + + + + | 0 |
| 532-533 | + + + + | 0 |
| 552-553 | + + + | 0 |

In a second round of mutagenesis, prompted by the observation that three morbilliviruses (MV, CDV, and RV) use SLAM as a cellular receptor, conserved residues or groups of residues were altered (FIG. 5). Two mutants were identified that selectively lost SLAM-dependent fusion (Table 2; 529-530 and 532-533), together with a mutant that lost CD46-dependant fusion (527-528). All mutagenized residues, as well as nearby residues not considered in the initial mutagenesis, were then mutated individually. Functional screening of these mutants resulted in the identification of single residues that selectively interacted with one or the other receptor. Individual mutation of residues 431, 451, 481, and 527 reduced CD46 binding, while mutation of residues 529, 530, 533, and 553 resulted in reduced SLAM binding. Again, these results demonstrate that the CD46-dependent fusion and SLAM-dependent fusion activities of an H polypeptide can be separated.

Nucleic acids encoding the four H polypeptides containing individual amino acid mutations (Y529A, D530A, R533A and Y553A) were imported into MV-Edm based infectious cDNAs; the Y553A mutant was imported into a "standard" genome whereas the other three mutants were introduced into a genome with an additional transcription unit expressing GFP. Viruses were recovered from all mutants, grown in Vero cells, and then used for parallel infection of Vero cells (CD46 positive, SLAM negative) or B95a cells (CD46 negative, SLAM positive).

Figure 6:
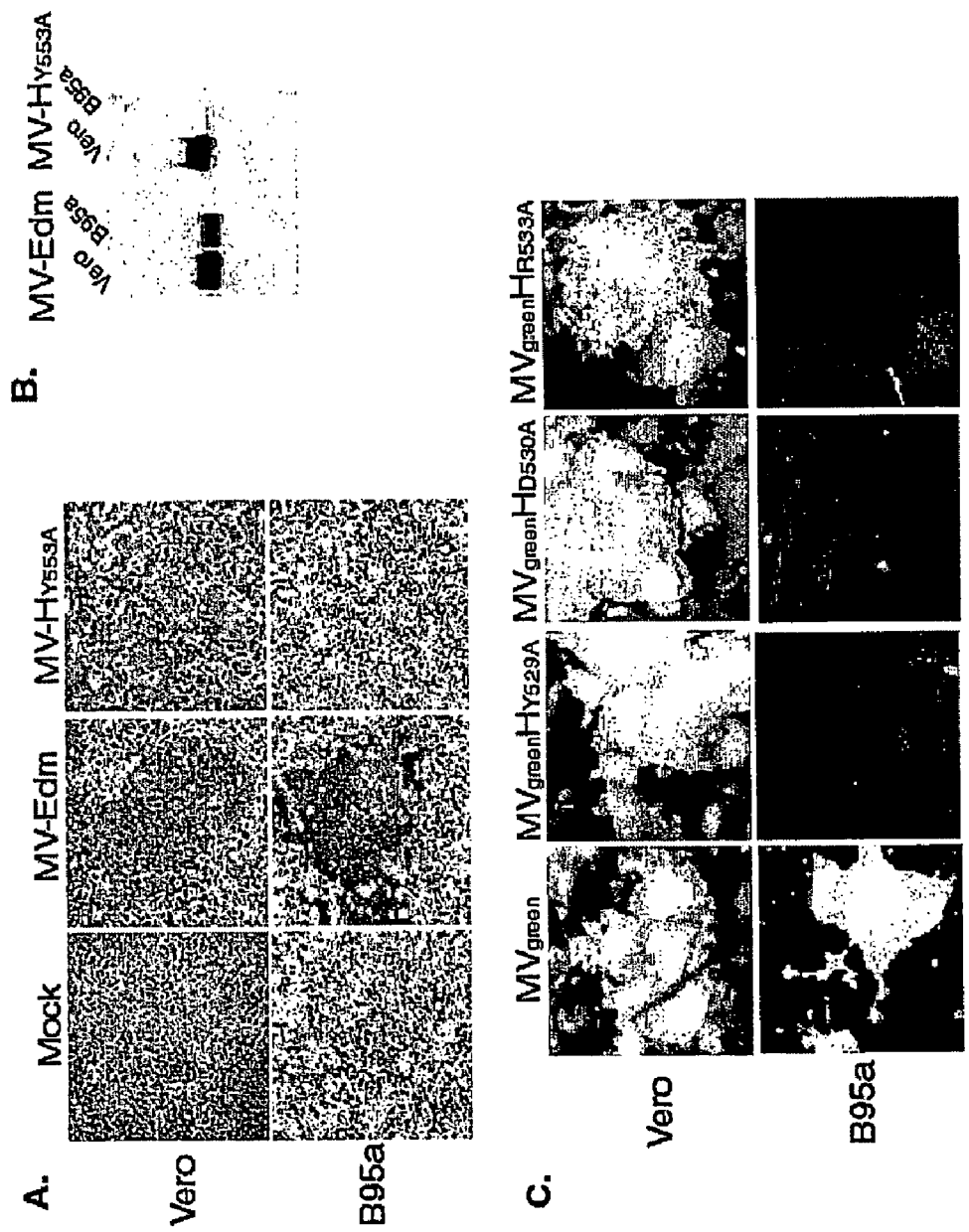

FIG. 6A shows a phase contrast analysis of cells mock-infected or infected with MV-Edm or MV-H$_{Y553A}$. MV-H$_{Y553A}$ formed syncytia on Vero cells but not on B95a cells. FIG. 6B shows a Western blot of the viral H polypeptides produced in the corresponding infections. These data confirmed that the propagation of MV-H$_{Y553A}$ was selectively impaired in cells expressing only SLAM. FIG. 6C is a fluorescent micrograph showing GFP expression from MV$_{green}$, MV$_{green}$-H$_{Y529A}$, MV$_{green}$-H$_{D530A}$, and MV$_{green}$-H$_{R533A}$ in cells expressing either CD46 or SLAM. Again, propagation of the three mutants was restricted in B95a (SLAM⁺) cells, while they behaved similarly to the standard Edm virus in Vero cells.

Example 8

Dissemination and Pathogenesis of MV-Edm in a Genetically Modified Mouse Model

The generation of genetically modified mice that express human CD46 with human-like tissue specificity has allowed studies of dissemination of the attenuated MV-Edm strain in PBMC and in lymphatic organs of these animals. The transfer of a large human genomic segment to mice often results in the transfer of human-like tissue specificity of gene expression, likely because of the inclusion of the dominant control regions. This principle was exploited to construct CD46Ge mice, using a yeast artificial chromosome with a human genomic insert covering not only the 50 kb CD46 gene but also about 150 kilobases upstream and downstream from the gene. CD46Ge mice expressed human CD46 with human-like tissue specificity (Mrkic et al. (1998) *J. Virol.* 72:7420-7427). Mice in this strain have intact interferon systems and can rapidly clear infections. A second CD46 strain having a targeted mutation in one chain of the interferon receptor was generated (Ifnar$^{ko}$-CD46Ge). This mutation eliminates interferon α/β function and permits systemic dissemination of infectious particles.

The infection of different types of PBMC was monitored in these two mouse strains. Mice were inoculated intranasally (i.n.) or intraperitoneally (i.p.) with MV-Edm. PMBC were isolated and examined for infection. In both strains, MV-Edm preferentially infected monocytes (F4/80 positive cells), but also infected B cells (B220 positive cells) and CD4 T cells (Table 3). Infection of CD8 T cells was minimal. In addition, large syncytia were found in the lymph nodes of the Ifnar$^{ko}$-CD46Ge mice, which stained positive for viral RNA and macrophage surface markers. These results indicate that it is possible to characterize the early phases of MV-Edm infection in genetically modified mice expressing CD46.

TABLE 3

MV H polypeptide expression in PBMC of mice inoculated with MV-Edm

| | Number of MV H polypeptide positive mice/total$^a$ | | |
|---|---|---|---|
| Cell | Ifnar$^{ko}$-CD46Ge | | CD46Ge |
| type | i.n. inoculated | i.p. inoculated | (i.p. inoculated) |
| F4/80⁺ | 7/9 (1.81 ± 1.02) | 4/5 (3.24 ± 1.86) | 6/7 (1.37 ± 0.63) |
| B220⁺ | 6/9 (0.58 ± 0.48) | 3/5 (0.78 ± 0.44) | 4/7 (0.67 ± 0.29) |
| CD4⁺ | 4/9 (0.62 ± 0.46) | 5/5 (0.99 ± 0.80) | 6/7 (0.54 ± 0.28) |
| CD8⁺ | 0/9 | 1/5 (0.67) | 0/7 |

$^a$The percentage of positive cells (mean ± standard deviation after background correction) is indicated in parenthesis; only positive animals were considered. On average, 1300 F4/80⁺ cells, 7600 B220⁺ cells, 4100 CD4⁺ T cells, and 2000 CD8⁺ T cells were counted. FACS analysis of CD46 expression on cells of eight mice revealed a mean fluorescence of 24 for F4/80⁺ cells, 30 for B220⁺ cells, 11 for CD4⁺ T cells, 5 for CD8⁺ T cells, and 0.1 for erythrocytes.

Production of mice expressing human SLAM with human-like tissue specificity. The strategy described above also is used to produce genetically modified mice expressing the SLAM receptor with human-like tissue specificity. Such a strain is useful to model acute MV infection of humans, since clinical MV strains bind to SLAM more efficiently than to CD46.

The human SLAM gene has been cloned on two bacterial artificial chromosomes, with GenBank accession numbers AC027082.3 (gene structure: CD84-SLAM-CD48) and AL355996.3 (gene structure: SLAM8-CD84-SLAM). Such BAC DNAs are used for oocyte microinjection. Alternatively, a YAC covering the SLAM gene is selected from the library used to identify the CD46 YAC (Hourcade et al. (1992) *Genomics* 12:289-300) and then is used for oocyte microinjection. Buffers containing NaCl and polyamines are used to compact the DNA and minimize shearing forces.

SLAMGe transgenic animals are produced by nuclear injection of fertilized oocytes from C57B6/J mice. Microinjection buffer, again containing NaCl and polyamines but compatible with oocyte survival, is used to dialyze BAC DNA before microinjection. Oocytes are transferred to pseudopregnant foster mothers and the pups are screened by PCR using primer pairs covering both ends of the SLAM insert. The integrity of the insert and the homozygosity of successive generations are tested by Southern blotting. Infection experiments are carried out with homozygous animals, according to the methods described herein.

MV replication typically is suboptimal in mouse cells, and therefore even transgenic mice expressing both CD46 and SLAM with human-like tissue specificity may allow only limited MV dissemination. This situation was remedied by crossing CD46Ge mice into an interferon type I (α/β) defective background (above). Similarly, strains are generated that not only express both SLAM and CD46, but also are defective in the interferon system (Ifnar$^{ko}$). This is achieved simply by crossing SLAMGe with CD46Ge-Ifnar$^{ko}$ mice. From this crossing three lines are selected: SLAMGe-CD46Ge, SLAMGe-CD46Ge-Ifnar$^{ko}$ and SLAMGe-Ifnar$^{ko}$.

Characterization of the dissemination and pathology of natural and recombinant MV strains in PBMC, in lymphoid organs, and systemically. The replication of MV-Edm in CD46Ge and CD46Ge-Ifnar$^{ko}$ mice (above) is used as a positive control for infection experiments with SLAMGe, SLAMGe-CD46Ge, and SLAMGe-CD46Ge-Ifnar$^{ko}$ animals. The experiments are conducted as described above (e.g., with intranasal and intraperitoneal inoculation and MOI of $10^5$ or $10^6$), using MV-Edm, MVEdm-H$_{wtF}$, and other viruses having mutated H polypeptides.

Systemic evaluation of viral dissemination and pathogenesis includes counting the number of PBMC to determine whether lymphopenia has occurred. In addition, the spleen, thymus, and lymph nodes are collected from all mice having positive PBMC and from a few mock-infected animals. Histological examination of these tissues includes hematoxylin-eosin staining to determine whether syncytia are present.

Viral replication in tissues also is monitored by immunohistochemistry and in situ hybridization. Detection of MV mRNA in situ is based on paraffin sections and a digoxigenin-labelled N mRNA probe. Antibodies are used to stain for cell differentiation markers: antibodies against CD45R/B220 to identify B cells; antibodies against CD3, CD4, and CD8 to identify T cells; antibodies against F4/80, MOMA1, and ERTR9 to identify macrophages; antibodies against 4C11 to identify follicular DC; and antibodies against NLDC145 to identify interdigitating DC.

It is hypothesized that T cells play a more important role in the dissemination of viruses with an H$_{wtF}$ polypeptide than in the dissemination of viruses with an H$_{Edm}$ polypeptide. This hypothesis is tested by characterizing dissemination of MV-Edm and MVEdm-H$_{wtF}$ in SLAMGe-CD46Ge and SLAMGe-CD46Ge-Ifnar$^{ko}$ using the methods described above. Recombinant MV strains with minimal SLAM binding allow more stringent experimental testing of the hypothesis that efficient dissemination in immune cells is SLAM-dependent. A simultaneous examination of propagation of a comparable MV with minimal CD46 binding provides insight into the relative importance of the two receptors for viral dissemination.

Non-invasive visualization (tracking) of MV infection in mice. If replication of a recombinant MV is high enough in the tissues (e.g., the lymph nodes or spleen) of an infected animal, infection is visualized by non-invasive methods that involve detection of a reporter enzyme. Different reporter genes are used to monitor the replication of recombinant MV in mice. Viruses expressing a chloramphenicol acetyl transferase (CAT) gene from an additional transcription unit were used to assess virus dissemination in protein extracts from different organs (Mrkic et al. supra). Viruses expressing GFP are ideally suited to follow (ex vivo or in vivo) infection of PBMC. A recombinant MV expressing the firefly luciferase protein (from pGL3 control vector; Promega, Madison, Wis.) also is used to infect tissues, which emit light upon substrate injection. Infected tissues are monitored in a living animal immobilized in a ChemiImager 5500 Imaging system (Alpha Innotech Corporation, San Leandro, Calif.), using a CCD camera.

Example 9

Antibody-targeted Cell Fusion

The measles H polypeptide is composed of a cytoplasmic tail, a transmembrane region, and six β-strands of β-propeller (FIG. 10A). In order to ablate the natural viral tropism, CD46 and SLAM binding sites were mutagenized. In addition, a single-chain antibody (scFv) against CD38, a myeloma cell marker, was used to introduce a new tropism. The resulting plasmids encoding an H polypeptide with a particular H polypeptide mutation (or combination of mutations) linked to a scFv against CD38 were co-transfected with a plasmid encoding an F polypeptide into Vero cells (CD46$^+$ cells), CHO-SLAM cells (SLAM$^+$ cells), or CHO-CD38 cells (CD38$^+$ cells). Once co-transfected, the cells were assessed for cell fusion by measuring the number of syncytia and the number of nuclei per syncytium (FIG. 10B).

Figure 12:
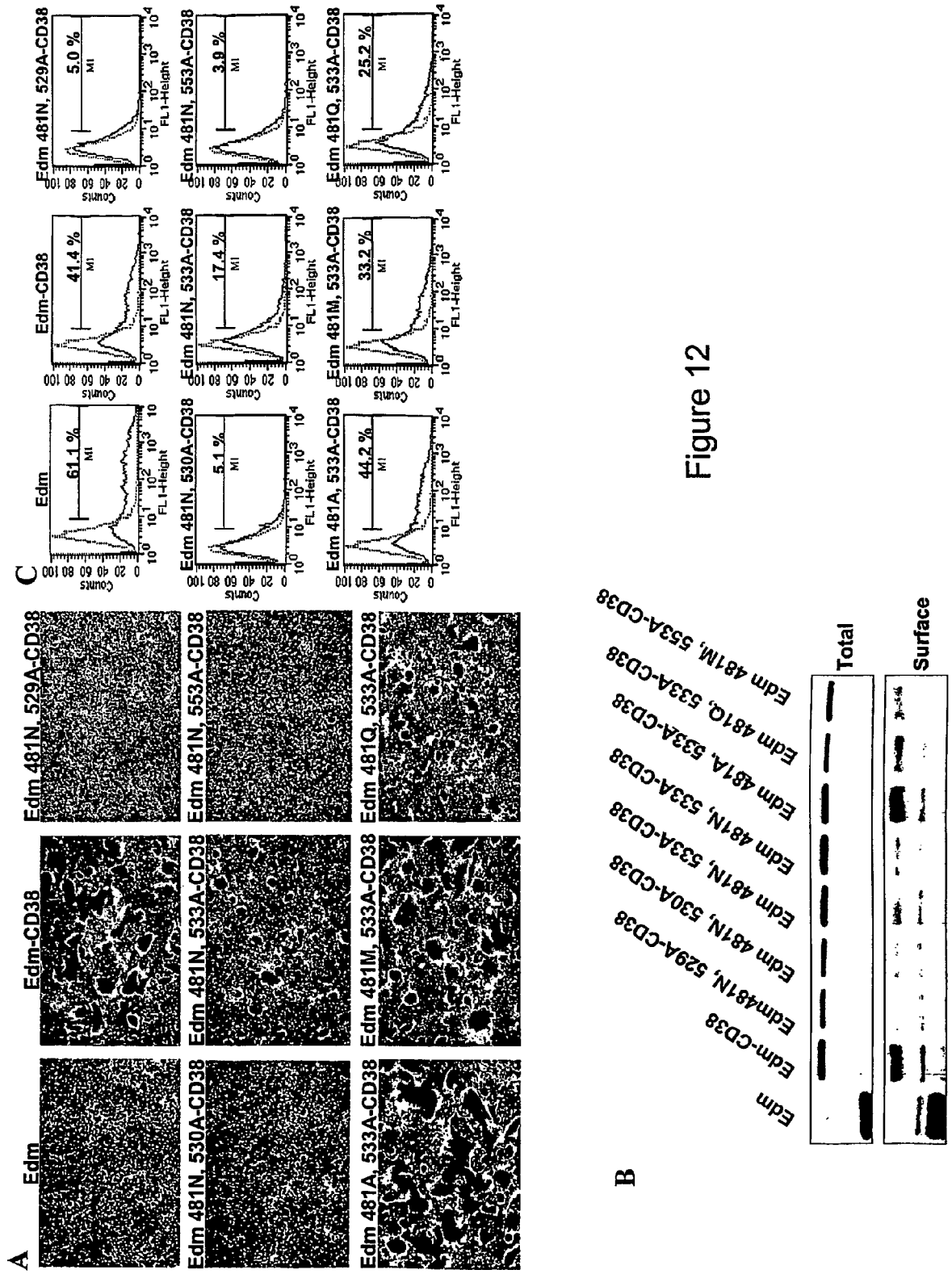

All three cells exhibited cell fusion when co-transfected with the Edm-CD38 plasmid and an F polypeptide-encoding plasmid, while no cell fusion was observed in CHO-CD38 cells when the Edm plasmid was used in place of the Edm-CD38 plasmid (FIG. 11). Chimeric H polypeptides with multiple 7 or 8 mutations lost the ability to induce cell fusion. A single mutation at position 527 resulted in a polypeptide that lost the ability to induce cell fusion in the tested cells. Double mutants at positions 431 and 533; 451 and 529; or 481 and 533 induced cell fusion in CHO-CD38 cells, but not Vero or CHO-SLAM cells. The level of syncytia formation exhibited in Vero cells, CHO-SLAM cells, and CHO-CD38 cells induced by other combinations of mutations is presented in FIG. 11. These results demonstrate that CD46$^+$ and SLAM$^+$ cells transfected with, for example, a plasmid encoding an H polypeptide with alanine residues at positions 481 and 533 (Edm-481A, 533A-CD38) do not form syncytia, while CD38$^+$ cells transfected with this plasmid do (FIG. 11). In addition, the 481A, 533A H polypeptide (Edm 481A, 533A-CD38) induced more cell fusion in CHO-CD38 cells than the amount induced by a wild type H polypeptide (Edm-CD38), the 481M, 533A H polypeptide (Edm 481M, 533A-CD38), and the 481Q, 533A H polypeptide (Edm 481Q, 533A-CD38) (FIG. 12A).

The amounts of total and surface-expressed H polypeptide in CHO-CD38 cells transfected with various H polypeptides were compared. No significant difference in total H polypeptide expression was observed between the unmodified H polypeptide (Edm), the scFv-CD38-H polypeptide (Edm-CD38), and the tested mutant H polypeptides (FIG. 12B). In contrast, the surface H polypeptide expression in CHO-CD38 cells dramatically differed among the H polypeptide mutants as shown in a western blot (FIG. 12B) as well as FACS analysis (FIG. 12C). In addition, the level of surface expression by each chimeric H polypeptide, except the unmodified H, was consistently in accord with the intensity of cell fusion activity. Taken together, these results indicate that (1) the amino acid at position 481 can regulate cell fusion and (2) the ability to induce cell fusion can depend on the ability of the H polypeptide to be expressed on the cell surface.

In a separate experiment, plasmids were constructed to encode the various mutated H polypeptides fused to a scFv that recognized either CD38, epidermal growth factor receptor (EGFR), or carcinoembryonic antigen (CEA) (Hammond et al., *J. Virol.*, 75 (5):2087-96 (2001) and Chester et al., *Lancet,* 343 (8895):455-6 (1994)). These plasmids were co-transfected with a plasmid encoding an F polypeptide into Vero cells (CD46$^+$ cells), CHO-CD46 cells (CD46$^+$ cells), CHO-SLAM cells (SLAM$^+$ cells), CHO-CD38 cells (CD38$^+$ cells), CHO-EGFR cells (EGFR$^+$ cells), or MC38-CEA cells (CEA$^+$ cells). Once co-transfected, the cells were assessed for cell fusion and cell viability.

Cell viability was measured as follows. Cells ($2\times10^4$/well in 96-well plate) were co-transfected with 0.25 µg of each plasmid DNA, and the cell viability was assessed by CellTiter96R AQueous Non-Radioactive Cell Proliferation Assay (promega) 36 hours post-transfection.

Figure 13:
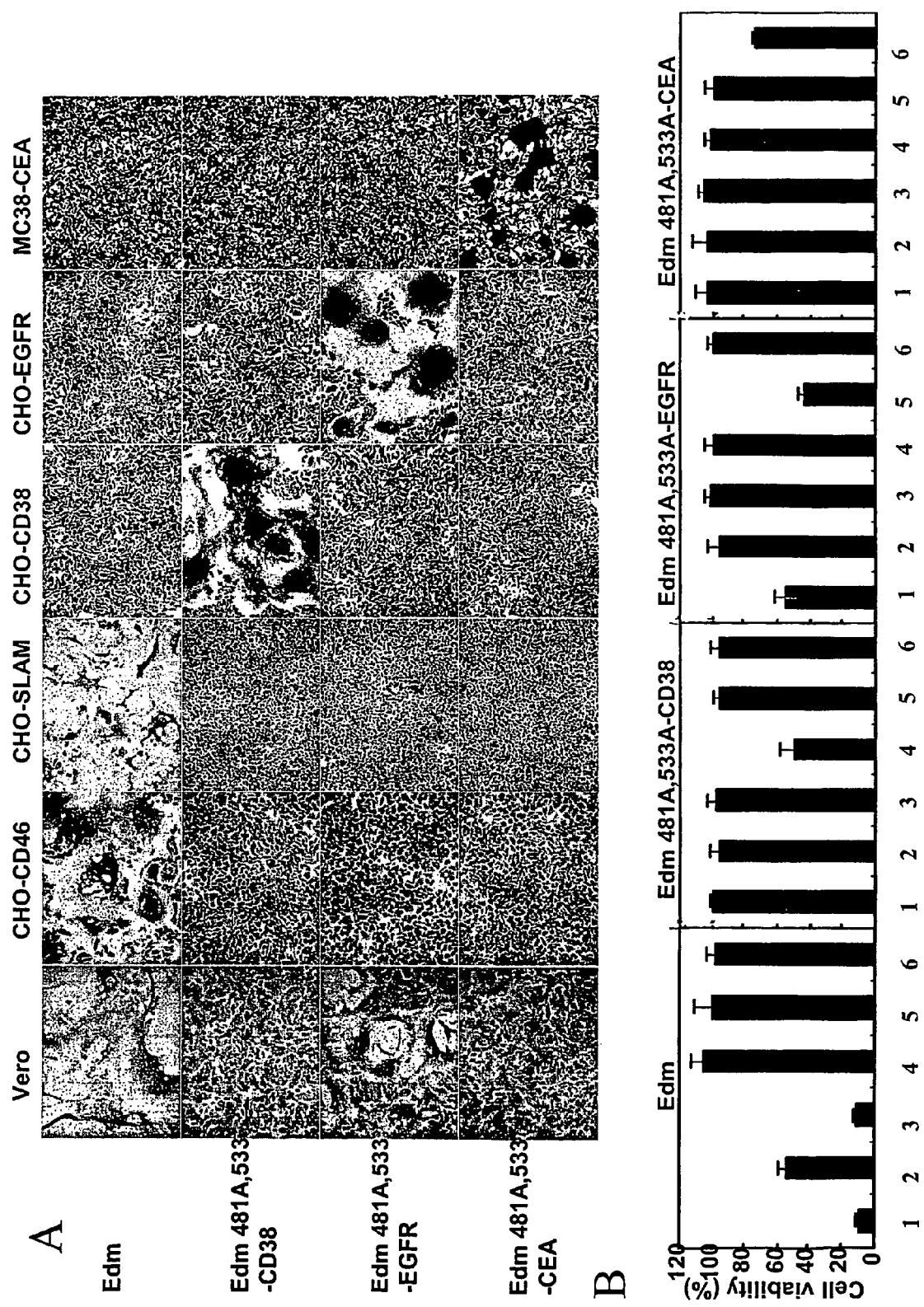

Vero cells, which are CD46$^+$, SLAM$^-$, CD38$^-$, EGFR$^+$, and CEA$^-$, exhibited cell fusion and reduced cell viability when transfected with either a plasmid encoding wild type H polypeptide (Edm) or a plasmid encoding a mutant H polypeptide fused to the scFv against EGFR (Edm 481A, 533A-EGFR) (FIGS. 13A and B). The CHO-CD46 cells, which are CD46$^+$, SLAM$^-$, CD38$^-$, EGFR$^-$, and CEA$^-$, exhibited cell fusion and reduced cell viability when transfected with a plasmid encoding wild type H polypeptide (Edm) (FIGS. 13A and B). The CHO-SLAM cells, which are CD46$^-$, SLAM$^+$, CD38$^-$, EGFR$^-$, and CEA$^-$, exhibited cell fusion and reduced cell viability when transfected with a plasmid encoding wild type H polypeptide (Edm) (FIGS. 13A and B). The CHO-CD38 cells, which are CD46$^-$, SLAM$^-$, CD38$^+$, EGFR$^-$, and CEA$^-$, exhibited cell fusion and reduced cell viability when transfected with a plasmid encoding a mutant H polypeptide fused to the scFv against CD38 (Edm 481A, 533A-CD38) (FIGS. 13A and B). The CHO-EGFR cells, which are CD46$^-$, SLAM$^-$, CD38$^-$, EGFR$^+$, and CEA$^-$, exhibited cell fusion and reduced cell viability when transfected with a plasmid encoding a mutant H polypeptide fused to the scFv against EGFR (Edm 481A, 533A-EGFR) (FIGS. 13A and B). The MC38-CEA cells, which are CD46$^-$, SLAM$^-$, CD38$^-$, EGFR$^-$, and CEA$^+$, exhibited cell fusion and reduced cell viability when transfected with a plasmid encoding a mutant H polypeptide fused to the scFv against CEA (Edm 481A, 533A-CEA) (FIGS. 13A and B). These results demonstrate that the recognition and binding of natural H polypeptides to their native receptors can be ablated and substituted by using other polypeptides (e.g., scFv) with high affinity to different specific receptors.

The site-directed mutagenesis was performed using the Quick-Change system (Stratagene) and the nucleic acid construct encoding the measles H polypeptide-scFv-CD38 (pCGHX α-CD38; Peng et al., Blood, 101 (7):2557-62 (2003)). The other scFv-displayed constructs were made by exchanging the scFv-CD38 fragment with each scFv fragment from EGFR (Schneider et al., J. Virol., 74 (21):9928-36 (2000)) or CEA (Hammond et al., J. Virol., 75 (5):2087-96 (2001)) in the Sfi I and Not I-digested site of pCGHX α-CD38. Cells ($8 \times 10^4$/well in 24-well plate) were co-transfected with 0.5 µg of plasmid DNA encoding an F polypeptide (Hammond et al., J. Virol., 75 (5):2087-96 (2001)) and 0.5 µg of a plasmid encoding the appropriate H polypeptide (wild-type or mutant) using Superfect (Qiagen). At 24 hours post-transfection, the degree of syncytia formation was scored and photographed.

The levels of H polypeptide total expression and surface expression were determined as follows. Cells ($4 \times 10^5$/well in 6-well plate) were transfected with the appropriate plasmid. After 24 hours, the transfected cells were washed two times with 1 mL of ice-cold phosphate-buffered saline (PBS), and surface polypeptides were labeled with biotin-7-NHS including Cellular Labeling kit (Roche) for 15 minutes at room temperature. The reaction was stopped by incubating $NH_4Cl$ (final concentration: 50 mM) for 15 minutes at 4° C. The cells were washed once, and treated with 500 µL of lysis buffer (50 mM Tris (pH 7.5), 1% Igepal CA-630 (Sigma), 1 mM EDTA, 150 mM sodium chloride, protease inhibitor cocktail (Sigma)) for 15 minutes at 4° C., and the lysates were subjected to centrifugation at 4° C. for 15 minutes at 12,000×g. Then, 20 µL of the resulting post-nuclear fraction was directly mixed with an equal volume of SDS loading buffer (130 mM Tris (pH 6.8), 20% glycerol, 10% SDS, 0.02% bromophenol blue, 100 mM DTT). These samples (40 µL) were fractionated on an 7.5% SDS-polyacrylamide gel, blotted to polyvinylidene difluoride membranes (Bio-rad), immunoblotted with anti-Flag M2 antibody conjugated to horseradish peroxidase, and subjected to enhanced chemiluminescence kit (Pierce) for detection of total H polypeptide. The biotinylated H polypeptide was immunoprecipitated using Immunoprecipitation kit (Roche). 50 µL of protein A-coated agarose beads was mixed with 350 µL of the postnuclear supernatant and 1 µL of anti-Flag M2 antibody (Sigma), followed by overnight incubation at 4° C. under rotation. The agarose beads were then washed three times prior to resuspension in 50 µL of loading buffer and boiling for 2 minutes at 100° C. to elute bound proteins. As described above, the samples (40 µL) were fractionated on an SDS-polyacrylamide gel, blotted to polyvinylidene difluoride membranes, and probed with peroxidase-coupled streptavidin (Roche), followed by enhanced chemiluminescence kit for detection of surface H polypeptides. Alternatively, the surface expression level of H polypeptides was detected by FACS analysis. Similarly, the cells 24 hours after transfection of the appropriate plasmid were washed twice with PBS and resuspended in ice-cold PBS containing 2% fetal bovine serum (FBS) at a concentration of $10^5$ cells/mL. The cells were then incubated for 60 minutes on ice with 1/150 final dilution of primary antibody ascites measles H polypeptide (Chemicon). Subsequently, the cells were washed with 2% FBS/PBS and incubated for an additional 30 minutes with 1/150 final dilution of FITC-conjugated goat anti-mouse IgG (Santa Cruz). After washing with 2% FBS/PBS, the cells were analyzed by flow cytometry using a FACScan system with CELLQuest software (Becton Dickinson).

Example 10

Engineered Viruses with Ablated CD46 and SLAM Binding can Infect CD38 Positive Cells Control viruses and viruses with ablated CD46 and SLAM binding were rescued and analyzed for the ability to infected different cells. In particular, the tropism of the new virus (MVgfpHAA αCD38) was compared against the parental virus MVgfpH αCD38 and the SLAM-ablated virus MVgfpHslam$^{ko}$ αCD38 on a panel of receptor positive cell lines. The MVgfpHAA αCD38 virus contains nucleic acid encoding an H polypeptide-scFv CD38 with the 481A and 533A mutations. The MVgfpHAA αCD38 virus infected CHO-CD38 cells, but not Vero, CHO-SLAM, CHO-EGFR, or CHO cells (Table 4). These results demonstrate that the natural tropism of the virus can be ablated and a new specificity domain can be used to redirect the viruses ability to infect cells.

TABLE 4

Number of plaque forming units/mL of virus.

| | MVgfpH αCD38 | MVgfpHslam$^{ko}$ αCD38 | MVgfpHAA αCD38 |
|---|---|---|---|
| Vero (CD46+) | $5.5 \times 10^5$* | $5.25 \times 10^5$** | <1 |
| CHO-SLAM | $1.0 \times 10^5$ | <1 | <1 |
| CHO-CD38 | $2.83 \times 10^4$ | $3.16 \times 10^4$ | $4 \times 10^5$ |
| CHO-EGFR | <1 | <1 | <1 |
| CHO | <1 | <1 | <1 |

*number of nuclei per syncytium >50
**number of nuclei per syncytium ~20

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated measles virus hemagglutinin (H) polypeptide, wherein mammalian SLAM+ cells comprising said H polypeptide and a fusion (F) polypeptide consisting of the amino acid sequence set forth in SEQ ID NO:8 fuse in a SLAM-dependent manner to a lesser extent than control mammalian SLAM+ cells comprising a test H polypeptide consisting of the amino acid sequence set forth in SEQ ID NO:1 and said F polypeptide, wherein said H polypeptide in combination with said F polypeptide comprises the ability to induce cell fusion, and wherein the amino acid sequence of said H polypeptide comprises at least one amino acid selected from the group consisting of:
   (i) an amino acid other than arginine at the position corresponding to position 533 of the amino acid sequence of SEQ ID NO:1, and
   (ii) an amino acid other than tyrosine at the position corresponding to position 553 of said amino acid sequence.

2. The polypeptide of claim 1, wherein said mammalian SLAM+ cells can fuse in a CD46-dependent manner.

3. The polypeptide of claim 2, wherein said polypeptide comprises a second amino acid sequence, and wherein said second amino acid sequence is attached to the carboxy-terminal portion of the amino acid sequence of said H polypeptide.

4. The polypeptide of claim 1, wherein a virus comprising said H polypeptide has the ability to enter cells in a CD46-dependent manner.

5. The polypeptide of claim 4, wherein said H polypeptide comprises a second amino acid sequence, and wherein said second amino acid sequence is attached to the carboxy-terminal portion of the amino acid sequence of said H polypeptide.

6. The polypeptide of claim 1, wherein mammalian CD46+ cells comprising said polypeptide and said F polypeptide fuse in a CD46-dependent manner to a lesser extent than control mammalian CD46+ cells comprising said test H polypeptide and said F polypeptide, wherein said polypeptide comprises a second amino acid sequence, and wherein said second amino acid sequence is attached to the carboxy-terminal portion of the amino acid sequence of said H polypeptide.

7. The polypeptide of claim 6, wherein the amino acid sequence of said H polypeptide comprises at least one amino acid selected from the group consisting of:
  (a) an amino acid other than phenylalanine at the position corresponding to position 431 of said amino acid sequence,
  (b) an amino acid other than valine at the position corresponding to position 451 of said amino acid sequence,
  (c) an amino acid other than tyrosine at the position corresponding to position 481 of said amino acid sequence, and
  (d) an amino acid other than alanine at the position corresponding to position 527 of said amino acid sequence.

8. The polypeptide of claim 7, wherein said the amino acid sequence of H polypeptide comprises at least two of (a), (b), (c), or (d) above.

9. The polypeptide of claim 7, wherein the amino acid sequence of said H polypeptide comprises at least three of (a), (b), (c), or (d) above.

10. The polypeptide of claim 7, wherein the amino acid sequence of said H polypeptide comprises (a), (b), (c), and (d).

11. The polypeptide of claim 6, wherein said mammalian CD46+ cells are Vero cells.

12. The polypeptide of claim 6, wherein said mammalian CD46+ cells exhibit no CD46-dependent fusion.

13. The polypeptide of claim 1, wherein said polypeptide comprises a second amino acid sequence, and wherein said second amino acid sequence is attached to the carboxy- terminal portion of the amino acid sequence of said H polypeptide.

14. The polypeptide of claim 13, wherein said second amino acid sequence is a single chain antibody amino acid sequence.

15. The polypeptide of claim 13, wherein said second amino acid sequence is a growth factor amino acid sequence.

16. An isolated measles virus hemagglutinin (H) polypeptide, wherein mammalian SLAM+ cells comprising said H polypeptide and a fusion (F) polypeptide consisting of the amino acid sequence set forth in SEQ ID NO:8 fuse in a SLAM-dependent manner to a lesser extent than control mammalian SLAM+ cells comprising a test H polypeptide consisting of the amino acid sequence set forth in SEQ ID NO:1 and said F polypeptide, wherein said H polypeptide in combination with said F polypeptide comprises the ability to induce cell fusion, and wherein the amino acid sequence of said H polypeptide comprises at least two amino acid selected from the group consisting of:
  (i) an amino acid other than tyrosine at the position corresponding to position 529 of the amino acid sequence of SEQ ID NO:1,
  (ii) an amino acid other than arginine at the position corresponding to position 533 of said amino acid sequence, and
  (iii) an amino acid other than tyrosine at the position corresponding to position 553 of said amino acid sequence.

17. The polypeptide of claim 1, wherein the amino acid sequence of said H polypeptide comprises an amino acid other than aspartic acid at the position corresponding to position 530 of said amino acid sequence.

18. An isolated measles virus hemagglutinin (H) polypeptide, wherein mammalian SLAM+ cells comprising said H polypeptide and a fusion (F) polypeptide consisting of the amino acid sequence set forth in SEQ ID NO:8 fuse in a SLAM-dependent manner to a lesser extent than control mammalian SLAM+ cells comprising a test H polypeptide consisting of the amino acid sequence set forth in SEQ ID NO:1 and said F polypeptide. wherein said H polypeptide in combination with said F polypeptide comprises the ability to induce cell fusion, and wherein the amino acid sequence of said H polypeptide comprises:
  (i) an amino acid other than tyrosine at the position corresponding to position 529 of the amino acid sequence of SEQ ID NO:1,
  (ii) an amino acid other than arginine at the position corresponding to position 533 of said amino acid sequence, and
  (iii) an amino acid other than tyrosine at the position corresponding to position 553 of said amino acid sequence.

19. The polypeptide of claim 1, wherein said mammalian SLAM+ cells exhibit no SLAM-dependent fusion.

20. The polypeptide of claim 1, wherein said mammalian SLAM+ cells are CHO-SLAM cells or B95 a cells.

21. The polypeptide of claim 1, wherein the amino acid sequence of said H polypeptide comprises an amino acid other than arginine at the position corresponding to position 533 of said amino acid sequence.

22. An isolated measles virus hemagglutinin (H) polypeptide, wherein mammalian SLAM+ cells comprising said H polypeptide and a fusion (F) polypeptide consisting of the amino acid sequence set forth in SEQ ID NO:8 fuse in a SLAM-dependent manner to a lesser extent than control mammalian SLAM+ cells comprising a test H polypeptide consisting of the amino acid sequence set forth in SEQ ID NO:1 and said F polypeptide, wherein said H polypeptide in combination with said F polypeptide comprises the ability to induce cell fusion, wherein said H polypeptide comprises an amino acid other than tyrosine at the position corresponding to position 481 of the amino acid sequence of SEQ ID NO: 1 and an amino acid other than arginine at the position aligning with position 533 of said amino acid sequence of SEQ ID NO:1, wherein said H polypeptide comprises a second amino acid sequence, and wherein said second amino acid sequence is attached to the carboxy-terminal portion of said H polypeptide.

23. The polypeptide of claim 22, wherein said second amino acid sequence is a single chain antibody amino acid sequence.

24. The polypeptide of claim 22, wherein said second amino acid sequence is a growth factor amino acid sequence.

25. An isolated virus comprising a measles virus hemagglutinin (H) polypeptide, wherein mammalian SLAM+ cells comprising said H polypeptide and a fusion (F) polypeptide consisting of the amino acid sequence set forth in SEQ ID NO:8 fuse in a SLAM-dependent manner to a lesser extent than control mammalian SLAM+ cells comprising a test H polypeptide consisting of the amino acid sequence set forth in SEQ ID NO:1 and said F polypeptide, wherein said H polypeptide in combination with said F polypeptide comprises the ability to induce cell fusion, and wherein the amino acid sequence of said H polypeptide comprises at least one amino acid selected from the group consisting of:
  (i) an amino acid other than arginine at the position corresponding to position 533 of the amino acid sequence of SEQ ID NO:1, and
  (ii) an amino acid other than tyrosine at the position corresponding to position 553 of said amino acid sequence.

26. The virus of claim 25, wherein said mammalian SLAM+ cells can fuse in a CD46-dependent manner.

27. The virus of claim 26, wherein said polypeptide comprises a second amino acid sequence, and wherein said second amino acid sequence is attached to the carboxy-terminal portion of the amino acid sequence of said H polypeptide.

28. The virus of claim 25, wherein said virus comprising said H polypeptide has the ability to enter cells in a CD46-dependent manner.

29. The virus of claim 28, wherein said H polypeptide comprises a second amino acid sequence, and wherein said second amino acid sequence is attached to the carboxy-terminal portion of the amino acid sequence of said H polypeptide.

30. The virus of claim 25, wherein mammalian CD46$^+$ cells comprising said polypeptide and said F polypeptide fuse in a CD46-dependent manner to a lesser extent than control mammalian CD46$^+$ cells comprising said test H polypeptide and said F polypeptide, wherein said polypeptide comprises a second amino acid sequence, and wherein said second amino acid sequence is attached to the carboxy-terminal portion of the amino acid sequence of said H polypeptide.

31. The virus of claim 30, wherein the amino acid sequence of said H polypeptide comprises at least one amino acid selected from the group consisting of:
(a) an amino acid other than phenylalanine at the position corresponding to position 431 of said amino acid sequence,
(b) an amino acid other than valine at the position corresponding to position 451 of said amino acid sequence,
(c) an amino acid other than tyrosine at the position corresponding to position 481 of said amino acid sequence, and
(d) an amino acid other than alanine at the position corresponding to position 527 of said amino acid sequence.

32. The virus of claim 31, wherein the amino acid sequence of said H polypeptide comprises at least two of (a), (b), (c), or (d) above.

33. The virus of claim 31, wherein the amino acid sequence of said H polypeptide comprises at least three of (a), (b), (c), or (d) above.

34. The virus of claim 31, wherein the amino acid sequence of said H polypeptide comprises (a), (b), (c), and (d).

35. The virus of claim 30, wherein said mammalian CD46$^+$ cells are Vero cells.

36. The virus of claim 30, wherein said mammalian CD46$^+$ cells exhibit no CD46-dependent fusion.

37. The virus of claim 25, wherein said polypeptide comprises a second amino acid sequence, and wherein said second amino acid sequence is attached to the carboxy-terminal portion of the amino acid sequence of said H polypeptide.

38. The virus of claim 37, wherein said second amino acid sequence is a single chain antibody amino acid sequence.

39. The virus of claim 37, wherein said second amino acid sequence is a growth factor amino acid sequence.

40. An isolated virus comprising a measles virus hemagglutinin (H) polypeptide, wherein mammalian SLAM$^+$ cells comprising said H polypeptide and a fusion (F) polypeptide consisting of the amino acid sequence set forth in SEQ ID NO:8 fuse in a SLAM-dependent manner to a lesser extent than control mammalian SLAM$^+$ cells comprising a test H polypeptide consisting of the amino acid sequence set forth in SEQ ID NO:1 and said F polypeptide, wherein said H polypeptide in combination with said F polypeptide comprises the ability to induce cell fusion, and wherein the amino acid sequence of said H polypeptide comprises at least two amino acid selected from the group consisting of:
(i) an amino acid other than tyrosine at the position corresponding to position 529 of the amino acid sequence of SEQ ID NO:1,
(ii) an amino acid other than arginine at the position corresponding to position 533 of said amino acid sequence, and
(iii) an amino acid other than tyrosine at the position corresponding to position 553 of said amino acid sequence.

41. The virus of claim 25, wherein the amino acid sequence of said H polypeptide comprises an amino acid other than aspartic acid at the position corresponding to position 530 of said amino acid sequence.

42. An isolated virus comprising a measles virus hemagglutinin (H) polypeptide, wherein mammalian SLAM$^+$ cells comprising said H polypeptide and a fusion (F) polypeptide consisting of the amino acid sequence set forth in SEQ ID NO:8 fuse in a SLAM-dependent manner to a lesser extent than control mammalian SLAM$^+$ cells comprising a test H polypeptide consisting of the amino acid sequence set forth in SEQ ID NO:1 and said F polypeptide, wherein said H polypeptide in combination with said F polypeptide comprises the ability to induce cell fusion, and wherein the amino acid sequence of said H polypeptide comprises:
(i) an amino acid other than tyrosine at the position corresponding to position 529 of the amino acid sequence of SEQ ID NO:1,
(ii) an amino acid other than arginine at the position corresponding to position 533 of said amino acid sequence, and
(iii) an amino acid other than tyrosine at the position corresponding to position 553 of said amino acid sequence.

43. The virus of claim 25, wherein said mammalian SLAM$^+$ cells exhibit no SLAM-dependent fusion.

44. The virus of claim 25, wherein said mammalian SLAM$^+$ cells are CHO-SLAM cells or B95a cells.

45. The virus of claim 25, wherein the amino acid sequence of said H polypeptide comprises an amino acid other than arginine at the position corresponding to position 533 of said amino acid sequence.

46. An isolated virus comprising a measles virus hemagglutinin (H) polypeptide, wherein mammalian SLAM$^+$ cells comprising said H polypeptide and a fusion (F) polypeptide consisting of the amino acid sequence set forth in SEQ ID NO:8 fuse in a SLAM-dependent manner to a lesser extent than control mammalian SLAM$^+$ cells comprising a test H polypeptide consisting of the amino acid sequence set forth in SEQ ID NO:1 and said F polypeptide, wherein said H polypeptide in combination with said F polypeptide comprises the ability to induce cell fusion, wherein said H polypeptide comprises an amino acid other than tyrosine at the position corresponding to position 481 of the amino acid sequence of SEQ ID NO:1 and an amino acid other than arginine at the position aligning with position 533 of said amino acid sequence of SEQ ID NO:1, wherein said H polypeptide comprises a second amino acid sequence, and wherein said second amino acid sequence is attached to the carboxy-terminal portion of said H polypeptide.

47. The virus of claim 46, wherein said second amino acid sequence is a single chain antibody amino acid sequence.

48. The virus of claim 46, wherein said second amino acid sequence is a growth factor amino acid sequence.

* * * * *

UNITED STATES PATENT AND TRADEMARK OFFICE
CERTIFICATE OF CORRECTION

PATENT NO. : 7,635,752 B2
APPLICATION NO. : 10/512627
DATED : December 22, 2009
INVENTOR(S) : Roberto Cattaneo It is certified that error appears in the above-identified patent and that said Letters Patent is hereby corrected as shown below:

Title Page item 57, Abstract, please delete "Control apparatus forcefully stops inverter and inverter when DC/DC converter is anomalously stopped. Additionally, when one of inverters is anomalously stopped while DC/DC converter is normal, control apparatus forcefully stops the other inverter. Then, when a recovery condition is satisfied after the other inverter is forcefully stopped, control apparatus recovers the other inverter." and insert --The invention provides nucleic acids, polypeptides, and viruses containing nucleic acids and/or polypeptides. The invention also provides methods for using viruses to treat cancer patients. Specifically, the invention provides nucleic acid molecules encoding viral hemagglutinin (H) polypeptides, viral H polypeptides, and viruses containing nucleic acids and/or H polypeptides. Such viruses are useful for treating cancer patients without causing immune suppression.-- therefor;

Column 54, line 5 (Claim 18), please delete "polypeptide." and insert --polypeptide,-- therefor.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,635,752 B2  
APPLICATION NO. : 10/512627  
DATED : December 22, 2009  
INVENTOR(S) : Cattaneo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1213 days.

Signed and Sealed this

Twenty-first Day of December, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 617
<212> TYPE: PRT
<213> ORGANISM: Measles virus

<400> SEQUENCE: 1

```
Met Ser Pro Gln Arg Asp Arg Ile Asn Ala Phe Tyr Lys Asp Asn Pro
 1               5                  10                  15

His Pro Lys Gly Ser Arg Ile Val Ile Asn Arg Glu His Leu Met Ile
             20                  25                  30

Asp Arg Pro Tyr Val Leu Leu Ala Val Leu Phe Val Met Phe Leu Ser
         35                  40                  45

Leu Ile Gly Leu Leu Ala Ile Ala Gly Ile Arg Leu His Arg Ala Ala
     50                  55                  60

Ile Tyr Thr Ala Glu Ile His Lys Ser Leu Ser Thr Asn Leu Asp Val
 65                  70                  75                  80

Thr Asn Ser Ile Glu His Gln Val Lys Asp Val Leu Thr Pro Leu Phe
                 85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415
```

```
Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
            450                 455                 460

Gly Val Ile Asn Thr Leu Glu Trp Ile Pro Arg Phe Lys Val Ser Pro
465                 470                 475                 480

Tyr Leu Phe Asn Val Pro Ile Lys Glu Ala Gly Glu Asp Cys His Ala
            485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
            515                 520                 525

Tyr Asp Thr Ser Arg Val Glu His Ala Val Tyr Tyr Val Tyr Ser
            530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
            565                 570                 575

Leu Trp Cys Arg His Phe Cys Val Leu Ala Asp Ser Glu Ser Gly Gly
            580                 585                 590

His Ile Thr His Ser Gly Met Glu Gly Met Gly Val Ser Cys Thr Val
            595                 600                 605

Thr Arg Glu Asp Gly Thr Asn Arg Arg
            610                 615

<210> SEQ ID NO 2
<211> LENGTH: 604
<212> TYPE: PRT
<213> ORGANISM: Canine distemper virus

<400> SEQUENCE: 2

Met Leu Ser Tyr Gln Asp Lys Val Gly Ala Phe Tyr Lys Asp Asn Ala
 1               5                  10                  15

Arg Ala Asn Ser Thr Lys Leu Ser Leu Val Thr Glu Glu His Gly Gly
            20                  25                  30

Arg Arg Pro Pro Tyr Leu Leu Phe Val Leu Leu Ile Leu Leu Val Gly
            35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
            85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
            115                 120                 125

Arg Glu Phe Asp Phe Arg Asp Leu His Trp Cys Ile Asn Pro Pro Ser
            130                 135                 140

Lys Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
```

-continued

```
                165                 170                 175
Gly Gly Arg Ser Asp Ile Phe Pro Pro His Arg Cys Ser Gly Ala Thr
            180                 185                 190

Thr Ser Val Gly Lys Val Phe Pro Leu Ser Val Ser Leu Ser Met Ser
            195                 200                 205

Leu Ile Ser Arg Thr Ser Glu Ile Ile Asn Met Leu Thr Ala Ile Ser
            210                 215                 220

Asp Gly Val Tyr Gly Lys Thr Tyr Leu Leu Val Pro Asp Asp Ile Glu
225                 230                 235                 240

Arg Glu Phe Asp Thr Gln Glu Ile Arg Val Phe Glu Ile Gly Phe Ile
            245                 250                 255

Lys Arg Trp Leu Asn Asp Met Pro Leu Leu Gln Thr Thr Asn Tyr Met
            260                 265                 270

Val Leu Pro Glu Asn Ser Lys Ala Lys Val Cys Thr Ile Ala Val Gly
            275                 280                 285

Glu Leu Thr Leu Ala Ser Leu Cys Val Glu Glu Ser Thr Val Leu Leu
            290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
            325                 330                 335

Val Ala His Pro Ser Met Glu Lys Ile His Ile Thr Asn His Arg Gly
            340                 345                 350

Phe Ile Lys Asp Ser Ile Ala Thr Trp Met Val Pro Ala Leu Ala Ser
            355                 360                 365

Glu Lys Gln Glu Glu Gln Lys Gly Cys Leu Glu Ser Ala Cys Gln Arg
            370                 375                 380

Lys Thr Tyr Pro Met Cys Asn Gln Thr Ser Trp Glu Pro Phe Gly Gly
385                 390                 395                 400

Arg Gln Leu Pro Ser Tyr Gly Arg Leu Thr Leu Pro Leu Asp Ala Ser
            405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
            435                 440                 445

Trp Leu Thr Ile Pro Pro Lys Asn Gly Thr Ile Val Gly Leu Ile Asn
            450                 455                 460

Lys Ala Gly Arg Gly Asp Gln Phe Thr Val Leu Pro His Val Leu Thr
465                 470                 475                 480

Phe Ala Pro Trp Glu Ser Ser Gly Asn Cys Tyr Leu Pro Ile Gln Thr
            485                 490                 495

Ser Gln Ile Ile Asp Arg Asp Val Leu Ile Glu Ser Asn Ile Val Val
            500                 505                 510

Leu Pro Thr Gln Ser Phe Arg Tyr Val Ile Ala Thr Tyr Asp Ile Ser
            515                 520                 525

Arg Ser Asp His Ala Ile Val Tyr Tyr Val Tyr Asp Pro Ile Arg Thr
            530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
            565                 570                 575

Gln Phe Tyr Arg Phe Glu Ala Asp Ile Ala Asn Ser Thr Thr Ser Val
            580                 585                 590
```

Glu Asn Leu Val Arg Ile Arg Phe Ser Cys Asn Arg
        595                 600

<210> SEQ ID NO 3
<211> LENGTH: 643
<212> TYPE: PRT
<213> ORGANISM: Rinderpest virus

<400> SEQUENCE: 3

Met Ser Ser Pro Arg Asp Arg Val Asn Ala Phe Tyr Lys Asp Asn Leu
 1               5                  10                  15

Gln Phe Lys Asn Thr Arg Val Val Leu Asn Lys Glu Gln Leu Leu Ile
            20                  25                  30

Glu Arg Pro Tyr Met Leu Leu Ala Val Leu Phe Val Met Phe Leu Ser
        35                  40                  45

Leu Val Gly Leu Leu Ala Ile Ala Gly Ile Arg Leu His Arg Ala Ala
    50                  55                  60

Val Asn Thr Ala Glu Ile Asn Ser Gly Leu Thr Thr Ser Ile Asp Ile
65                  70                  75                  80

Thr Lys Ser Ile Glu Tyr Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Thr Lys Phe Ile Ser Asp Lys Ile Lys Phe Leu Asn Pro Asp
        115                 120                 125

Lys Glu Tyr Asp Phe Arg Asp Ile Asn Trp Cys Ile Ser Pro Pro Glu
    130                 135                 140

Arg Ile Lys Ile Asn Tyr Asp Gln Tyr Cys Ala His Thr Ala Ala Glu
145                 150                 155                 160

Glu Leu Ile Thr Met Leu Val Asn Ser Ser Leu Ala Gly Thr Ser Val
                165                 170                 175

Leu Pro Thr Ser Leu Val Asn Leu Gly Arg Ser Cys Thr Gly Ser Thr
            180                 185                 190

Thr Thr Lys Gly Gln Phe Ser Asn Met Ser Leu Ala Leu Ser Gly Ile
        195                 200                 205

Tyr Ser Gly Arg Gly Tyr Asn Ile Ser Ser Met Ile Thr Ile Thr Glu
    210                 215                 220

Lys Gly Met Tyr Gly Ser Thr Tyr Leu Val Gly Lys His Asn Gln Gly
225                 230                 235                 240

Ala Arg Arg Pro Ser Thr Ala Trp Gln Arg Asp Tyr Arg Val Phe Glu
                245                 250                 255

Val Gly Ile Ile Arg Glu Leu Gly Leu Gly Thr Pro Val Phe His Met
            260                 265                 270

Thr Asn Tyr Leu Glu Leu Pro Arg Gln Pro Glu Leu Glu Ile Cys Met
        275                 280                 285

Leu Ala Leu Gly Glu Phe Lys Leu Ala Ala Leu Cys Leu Ala Asp Asn
    290                 295                 300

Ser Val Ala Leu His Tyr Gly Gly Leu Arg Asp Asp His Lys Ile Arg
305                 310                 315                 320

Phe Val Lys Leu Gly Val Trp Pro Ser Pro Ala Asp Ser Asp Thr Leu
                325                 330                 335

Ala Thr Leu Ser Ala Val Asp Pro Thr Leu Asp Gly Leu Tyr Ile Thr
            340                 345                 350

Thr His Arg Gly Ile Ile Ala Ala Gly Lys Ala Val Trp Val Val Pro

-continued

```
                355                 360                 365
Val Thr Arg Thr Asp Asp Gln Arg Lys Met Gly Gln Cys Arg Arg Glu
370                 375                 380

Ala Cys Arg Glu Lys Pro Pro Phe Cys Asn Ser Thr Asp Trp Glu
385                 390                 395                 400

Pro Leu Glu Ala Gly Arg Ile Pro Ala Tyr Gly Ile Leu Thr Ile Arg
                405                 410                 415

Leu Gly Leu Ala Asp Lys Leu Lys Leu Thr Ile Ile Ser Glu Phe Gly
                420                 425                 430

Pro Leu Ile Thr His Asp Ser Gly Met Asp Leu Tyr Thr Pro Leu Asp
                435                 440                 445

Gly Asn Glu Tyr Trp Leu Thr Ile Pro Pro Leu Gln Asn Ser Ala Leu
450                 455                 460

Gly Thr Val Asn Thr Leu Val Leu Glu Pro Ser Leu Lys Ile Ser Pro
465                 470                 475                 480

Asn Ile Leu Thr Leu Pro Ile Arg Ser Gly Gly Gly Asp Cys Tyr Thr
                485                 490                 495

Pro Thr Tyr Leu Ser Asp Leu Ala Asp Asp Asp Val Lys Leu Ser Ser
                500                 505                 510

Asn Leu Val Ile Leu Pro Ser Arg Asn Leu Gln Tyr Val Ser Ala Thr
                515                 520                 525

Tyr Asp Thr Ser Arg Val Glu His Ala Ile Val Tyr Tyr Ile Tyr Ser
                530                 535                 540

Ala Gly Arg Leu Ser Ser Tyr Tyr Pro Val Lys Leu Pro Ile Lys
545                 550                 555                 560

Gly Asp Pro Val Ser Leu Gln Ile Gly Cys Phe Pro Trp Gly Leu Lys
                565                 570                 575

Leu Trp Cys His His Phe Cys Ser Val Ile Asp Ser Gly Thr Arg Lys
                580                 585                 590

Gln Val Thr His Thr Gly Ala Val Gly Ile Glu Ile Thr Cys Asn Ser
                595                 600                 605

Arg Gln Cys Leu Gly Pro Thr Arg Ser Arg Arg Pro Gly Pro Pro Thr
610                 615                 620

Ala Val Gly Pro Gly Thr Ala Leu His His Ala Asp Ser Phe Gln Tyr
625                 630                 635                 640

Tyr His Tyr

<210> SEQ ID NO 4
<211> LENGTH: 237
<212> TYPE: PRT
<213> ORGANISM: Measles virus

<400> SEQUENCE: 4

Cys Phe Gln Gln Ala Cys Lys Gly Lys Ile Gln Ala Leu Cys Glu Asn
1               5                   10                  15

Pro Glu Trp Ala Pro Leu Lys Asp Asn Arg Ile Pro Ser Tyr Gly Val
                20                  25                  30

Leu Ser Val Asp Leu Ser Leu Thr Val Glu Leu Lys Ile Lys Ile Ala
                35                  40                  45

Ser Gly Phe Gly Pro Leu Ile Thr His Gly Ser Gly Met Asp Leu Tyr
                50                  55                  60

Lys Ser Asn His Asn Asn Val Tyr Trp Leu Thr Ile Pro Pro Met Lys
65                  70                  75                  80

Asn Leu Ala Leu Gly Val Ile Asn Thr Leu Glu Trp Ile Pro Arg Phe
```

```
                    85                  90                  95
Lys Val Ser Pro Tyr Leu Phe Thr Val Pro Ile Lys Glu Ala Gly Glu
                100                 105                 110

Asp Cys His Ala Pro Thr Tyr Leu Pro Ala Glu Val Asp Gly Asp Val
            115                 120                 125

Lys Leu Ser Ser Asn Leu Val Ile Leu Pro Gly Gln Asp Leu Gln Tyr
        130                 135                 140

Val Leu Ala Thr Tyr Asp Thr Ser Arg Val Glu His Ala Val Val Tyr
145                 150                 155                 160

Tyr Val Tyr Ser Pro Ser Arg Ser Phe Ser Tyr Phe Pro Phe Arg
                165                 170                 175

Leu Pro Ile Lys Gly Val Pro Ile Glu Leu Gln Val Glu Cys Phe Thr
            180                 185                 190

Trp Asp Gln Lys Leu Trp Cys Arg His Phe Cys Val Leu Ala Asp Ser
        195                 200                 205

Glu Ser Gly Gly His Ile Thr His Ser Gly Met Val Gly Met Gly Val
210                 215                 220

Ser Cys Thr Val Thr Arg Glu Asp Gly Thr Asn Arg Arg
225                 230                 235

<210> SEQ ID NO 5
<211> LENGTH: 228
<212> TYPE: PRT
<213> ORGANISM: Canine distemper virus

<400> SEQUENCE: 5

Cys Leu Glu Ser Ala Cys Gln Arg Lys Thr Tyr Pro Met Cys Asn Gln
1               5                   10                  15

Ala Ser Trp Glu Pro Phe Gly Gly Arg Gln Leu Pro Ser Tyr Gly Arg
            20                  25                  30

Leu Thr Leu Pro Leu Asp Ala Ser Val Asp Leu Gln Leu Asn Ile Ser
        35                  40                  45

Phe Thr Tyr Gly Pro Val Ile Leu Asn Gly Asp Gly Met Asp Tyr Tyr
    50                  55                  60

Glu Ser Pro Leu Leu Asn Ser Gly Trp Leu Thr Ile Pro Pro Lys Asp
65                  70                  75                  80

Gly Thr Ile Ser Gly Leu Ile Asn Lys Ala Gly Arg Gly Asp Gln Phe
                85                  90                  95

Thr Val Leu Pro His Val Leu Thr Phe Ala Pro Arg Glu Ser Ser Gly
            100                 105                 110

Asn Cys Tyr Leu Pro Ile Gln Thr Ser Gln Ile Arg Asp Arg Asp Val
        115                 120                 125

Leu Ile Glu Ser Asn Ile Val Val Leu Pro Thr Gln Ser Ile Arg Tyr
    130                 135                 140

Val Ile Ala Thr Tyr Asp Ile Ser Arg Ser Asp His Ala Ile Val Tyr
145                 150                 155                 160

Tyr Val Tyr Asp Pro Ile Arg Thr Ile Ser Tyr Thr His Pro Phe Arg
                165                 170                 175

Leu Thr Thr Lys Gly Arg Pro Asp Phe Leu Arg Ile Glu Cys Phe Val
            180                 185                 190

Trp Asp Asp Asn Leu Trp Cys His Gln Phe Tyr Arg Phe Glu Ala Asp
        195                 200                 205

Ile Ala Asn Ser Thr Thr Ser Val Glu Asn Leu Val Arg Ile Arg Phe
    210                 215                 220
```

```
Ser Cys Asn Arg
225

<210> SEQ ID NO 6
<211> LENGTH: 229
<212> TYPE: PRT
<213> ORGANISM: Rinderpest virus

<400> SEQUENCE: 6

Cys Arg Arg Glu Ala Cys Arg Glu Lys Pro Pro Phe Cys Asn Ser
  1               5                  10                  15

Thr Asp Trp Glu Pro Leu Glu Ala Gly Arg Ile Pro Ala Tyr Gly Ile
             20                  25                  30

Leu Thr Ile Arg Leu Gly Leu Ala Asp Lys Leu Lys Leu Thr Ile Ile
                 35                  40                  45

Ser Glu Phe Gly Pro Leu Ile Thr His Asp Ser Gly Met Asp Leu Tyr
 50                  55                  60

Thr Pro Leu Asp Gly Asn Glu Tyr Trp Leu Thr Ile Pro Pro Leu Gln
 65                  70                  75                  80

Asn Ser Ala Leu Gly Thr Val Asn Thr Leu Val Leu Glu Pro Ser Leu
                 85                  90                  95

Lys Ile Ser Pro Asn Ile Leu Thr Leu Pro Ile Arg Ser Gly Gly Gly
             100                 105                 110

Asp Cys Tyr Thr Pro Thr Tyr Leu Ser Asp Leu Ala Asp Asp Asp Val
         115                 120                 125

Lys Leu Ser Ser Asn Leu Val Ile Leu Pro Ser Arg Asn Leu Gln Tyr
130                 135                 140

Val Ser Ala Thr Tyr Asp Thr Ser Arg Val Glu His Ala Ile Val Tyr
145                 150                 155                 160

Tyr Ile Tyr Ser Ala Gly Arg Leu Ser Ser Tyr Tyr Pro Val Lys
                 165                 170                 175

Leu Pro Ile Lys Gly Asp Pro Val Ser Leu Gln Ile Gly Cys Phe Pro
                 180                 185                 190

Trp Gly Leu Lys Leu Trp Cys His His Phe Cys Ser Val Ile Asp Ser
                 195                 200                 205

Gly Thr Arg Lys Gln Val Thr His Thr Gly Ala Val Gly Ile Glu Ile
             210                 215                 220

Thr Cys Asn Ser Arg
225

<210> SEQ ID NO 7
<211> LENGTH: 228
<212> TYPE: PRT
<213> ORGANISM: Canine distemper virus

<400> SEQUENCE: 7

Cys Leu Glu Ser Ala Cys Gln Arg Lys Thr Tyr Pro Met Cys Asn Gln
  1               5                  10                  15

Ala Ser Trp Glu Pro Phe Gly Gly Arg Gln Leu Pro Ser Tyr Gly Arg
             20                  25                  30

Leu Thr Leu Pro Leu Asp Ala Ser Val Asp Leu Gln Leu Asn Ile Ser
                 35                  40                  45

Phe Thr Tyr Gly Pro Val Ile Leu Asn Gly Asp Gly Met Asp Tyr Tyr
 50                  55                  60

Glu Ser Pro Leu Leu Asn Ser Gly Trp Leu Thr Ile Pro Pro Lys Asp
 65                  70                  75                  80
```

```
Gly Thr Ile Ser Gly Leu Ile Asn Lys Ala Gly Arg Gly Asp Gln Phe
                85                  90                  95

Thr Val Leu Pro His Val Leu Thr Phe Ala Pro Arg Glu Ser Ser Gly
            100                 105                 110

Asn Cys Tyr Leu Pro Ile Gln Thr Ser Gln Ile Arg Asp Arg Asp Val
            115                 120                 125

Leu Ile Glu Ser Asn Ile Val Val Leu Pro Thr Gln Ser Ile Arg Tyr
130                 135                 140

Val Ile Ala Thr Tyr Asp Ile Ser Arg Ser Asp His Ala Ile Val Tyr
145                 150                 155                 160

Tyr Val Tyr Asp Pro Ile Arg Thr Ile Ser Tyr Thr His Pro Phe Arg
                165                 170                 175

Leu Thr Thr Lys Gly Arg Pro Asp Phe Leu Arg Ile Glu Cys Phe Val
            180                 185                 190

Trp Asp Asp Asn Leu Trp Cys His Gln Phe Tyr Arg Phe Glu Ala Asp
            195                 200                 205

Ile Ala Asn Ser Thr Thr Ser Val Glu Asn Leu Val Arg Ile Arg Phe
210                 215                 220

Ser Cys Asn Arg
225

<210> SEQ ID NO 8
<211> LENGTH: 553
<212> TYPE: PRT
<213> ORGANISM: Measles virus

<400> SEQUENCE: 8

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
            35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
            115                 120                 125

Ala Thr Ala Ala Gln Ile Thr Ala Gly Ile Ala Leu His Gln Ser Met
130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
            195                 200                 205

Leu Leu Arg Tyr Tyr Thr Glu Ile Leu Ser Leu Phe Gly Pro Ser Leu
210                 215                 220
```

```
Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550

<210> SEQ ID NO 9
<211> LENGTH: 1853
<212> TYPE: DNA
<213> ORGANISM: Measles virus

<400> SEQUENCE: 9
atgtcaccac aacgagaccg gataaatgcc ttctacaaag ataaccccca tcccaaggga      60
agtaggatag tcattaacag agaacatctt atgattgata gaccttatgt tttgctggct     120
gttctgtttg tcatgtttct gagcttgatc gggttgctag ccattgcagg aattcgactt     180
catcgggcag ccatctacac cgcagagatc cataaaagcc tcagcaccaa tctagatgta     240
```

```
actaactcaa tcgagcatca ggtcaaggac gtgctgacac cactcttcaa aatcatcggt    300
gatgaagtgg gcctgaggac acctcagaga ttcactgacc tagtgaaatt catctctgac    360
aagattaaat tccttaatcc ggatagggag tacgacttca gagatctcac ttggtgtatc    420
acccgccaga gagaatcaaa ttggattatg atcaatactg tgcagatgtg gctgctgaag    480
agctcatgaa tgcattggtg aactcaactc tactggagac cagaacaacc aatcagttcc    540
tagctgtctc aaagggaaac tgctcagggc ccactacaat cagaggtcaa ttctcaaaca    600
tgtcgctgtc cctgttagac ttgtatttag gtcgaggtta caatgtgtca tctatagtca    660
ctatgacatc ccagggaatg tatggggaa cttacctagt ggaaaagcct aatctgagca    720
gcaaaaggtc agagttgtca caactgagca tgtaccgagt gtttgaagta ggtgttatca    780
gaaatccggg tttgggggct ccggtgttcc atatgacaaa ctatcttgag caaccagtca    840
gtaatgatct cagcaactgt atggtggctt gggggagct caaactcgca gccctttgtc    900
acggggaaga ttctatcaca attccctatc agggatcagg aaaggtgtc agcttccagc    960 tcgtcaagct aggtgtctgg aaatccccaa ccgacatgca atcctgggtc cccttatcaa   1020
cggatgatcc agtgatagac aggctttacc tctcatctca cagaggtgtt atcgctgaca   1080
atcaagcaaa atgggctgtc ccgacaaaca gaacagatga caagttgcga atggagacat   1140
gcttccaaca ggcgtgtaag ggtaaaatcc aagcactctg cgagaatccc gagtgggcac   1200
cattgaagga taacaggatt ccttcatacg gggtcttgtc tgttgatctg agtctgacag   1260
ttgagcttaa aatcaaaatt gcttcgggat tcgggccatt gatcacacac ggttcaggga   1320
tggacctata caaatccaac cacaacaatg tgtattggct gactatcccg ccaatgaaga   1380
acctagcctt aggtgtaatc aacacattgg agtggatacc gagattcaag gttagtccct   1440
acctcttcaa tgtcccaatt aaggaagcag gcgaagactg ccatgcccca acatacctac   1500
ctgcggaggt ggatggtgat gtcaaactca gttccaatct ggtgattcta cctggtcaag   1560
atctccaata tgttttggca acctacgata cttccagggt tgaacatgct gtggtttatt   1620
acgtttacag cccaagccgc tcattttctt acttttatcc ttttaggttg cctataaagg   1680
gggtccccat cgaattacaa gtggaatgct tcacatggga ccaaaaactc tggtgccgtc   1740
acttctgtgt gcttgcggac tcagaatctg gtggacatat cactcactct gggatggagg   1800
gcatgggagt cagctgcaca gtcacccggg aagatggaac caatcgcaga tag            1853

<210> SEQ ID NO 10
<211> LENGTH: 1814
<212> TYPE: DNA
<213> ORGANISM: Canine distemper virus

<400> SEQUENCE: 10
atgctctcct accaagacaa ggtgggtgcc ttctacaagg ataatgcaag agccaattca     60
accaagctgt ccttagtgac agaagaacat ggggggcagga gaccacctta tttgttgttt    120
gtccttctca tcttattggt tggaatcctg gccttgcttg ctatcactgg agttcgattt    180
caccaagtat caactagcaa tatggaattt agcagattgc tgaaagagga tatggagaaa    240
tcagaggccg tacatcacca agtcatagat gtcttgacac cgctcttcaa gattattgga    300
gatgagattg ggttacggtt gccacaaaag ctaaacgaga tcaaacaatt tatccttcaa    360
aagacaaatt tcttcaatcc gaacagagaa ttcgacttcc gcgatctcca ctggtgcatt    420
aacccgccta gtaaggtcaa ggtgaatttt actaattact gtgagtcaat tgggatcaga    480
```

```
aaagctattg catcggcagc aaatcctatc cttttatcag ccctatctgg gggcagaagt      540
gacatattcc caccacacag atgcagtgga gctactactt cagtaggcaa agttttcccc      600
ctatcagtct cattatccat gtctttgatc tcaagaacct cagagataat caatatgctg      660
accgctatct cagacggcgt gtatggcaaa acttacttgc tagtgcctga tgatatagaa      720
agagagttcg acactcaaga gattcgagtc tttgaaatag ggttcatcaa aggtggctg       780 aatgacatgc cattactcca aacaaccaac tatatggtac tcccggagaa ttccaaagcc      840
aaggtatgta ctatagcagt gggtgagttg acactggctt ccttgtgtgt agaagagagc      900
actgtattat tatatcatga cagcagtggt tcacaagatg gtattctagt agtgacactg      960
gggatatttt gggcaacacc tatggatcac attgaggaag tgatacctgt cgctcaccca     1020
tcaatggaga aaatacatat aacaaaccac cgtggtttta taaaagattc aattgcaacc     1080
tggatggtgc ctgccctggc ctctgagaaa caagaagaac aaaaaggttg tctggagtca     1140
gcttgtcaaa gaaaaaccta ccccatgtgc aaccaaacgt catgggaacc cttcggagga     1200
agacagttgc catcttatgg gcggttgaca ttacctctag atgcaagtgt tgaccttcaa     1260
cttaacatat cgttcacata cggtccggtc atactgaatg agatggtat ggattattat      1320 gaaagcccac ttttgaactc cggatggctt accattcctc ccaaaaacgg aacaatcgtt     1380
ggattgataa acaaagcagg tagaggagac cagttcactg tactccccca tgtgttaaca     1440
tttgcgcctt gggaatcaag tggaaattgt tatttaccta ttcaaacatc tcaaattata     1500
gatagagatg tcctcattga gtccaatata gtggtgttgc ctacacagag ttttagatat     1560
gtcatagcaa cgtatgacat atcacgaagt gatcatgcga ttgtttatta tgtttatgac     1620
ccaatccgga cgatttctta tacgcaccca tttagactaa ctaccaaggg tagacctgat     1680
ttcctaagga ttgaatgttt tgtgtgggat gacaatttgt ggtgtcacca attttacaga     1740
tcgaggctga catcgccaac tctacaacca gtgttgagaa tttagtccgt ataagattct     1800
catgtaaccg ttaa                                                       1814
```

<210> SEQ ID NO 11
<211> LENGTH: 1951
<212> TYPE: DNA
<213> ORGANISM: Rinderpest virus

<400> SEQUENCE: 11

```
aggatgcaag atcatccacc atgtcctccc caagagacag ggtcaatgcc ttctacaaag       60
acaacctcca atttaagaac actcgagtgg ttcttaataa agagcagctc ctgatagaaa      120
ggccttacat gttgctggcg gtgctgtttg ttatgttcct gagcctagtg gggctgttgg      180
ccattgcagg tatcagactc caccgagctg ctgtcaacac agcagagatc aacagtggtc      240
tgacgacaag cattgatatt accaagtcta ttgagtacca ggtcaaggac gtcttaactc      300
ccctcttcaa ataattgga gatgaggcg ggctgaggac acctcagaga ttcacagatc        360
tgactaaatt catatcagac aagattaagt tccttaaccc tgataaagag tacgacttca      420
gggatattaa ctggtgcatc agtccccag agagaatcaa gattaattat gatcagtatt       480
gtgctcacac agctgctgag gagctgataa ctatgctggt caattcgtct ctggcaggta      540
cttcggtact accgacatca ttagtcaact gggggaggag ctgtaccggg tccacaacga      600
ctaaaggtca attctctaac atgtcattgg ctctttcagg atatactca ggtcgtggct       660 acaatatttc atccatgata acaatcactg agaaaggcat gtacgaagc acttatctag      720 tcgggaaaca taatcaggga gccaggaggc caagcactgc ttggcaacgg gattaccgag      780
```

```
tctttgaagt aggcataatt agagaactag gactgggcac accagtgttt catatgacaa      840
actacctgga gctcccaaga cagccggaat tggagatctg catgctagct ctaggagagt      900
caaattagct gccctctgct tagctgataa ctctgtcgca ctgcattacg gggggttaag      960
ggacgaccac aagatcaggt ttgtcaaact gggagtatgg ccatcaccag ccgactcaga     1020
caccctggcc actctttcag cagtagatcc gaccttggat gggctctata tcacaactca     1080
taggggaatc atagctgcag ggaaggccgt atgggtcgtc cctgtgacga aacagatga      1140 ccaaaggaaa atgggacagt gccgccgaga ggcttgtcga gagaaaccac caccttctg      1200 taacagtaca gattgggagc cattagaggc cggccgtata ccggcatatg gaatactaac     1260
tatcaggctg gggctggctg ataagctgaa attgaccata atttcagaat ttggtccctt     1320
gatcacacat gactcaggga tggacttata cacccactt gacggtaatg agtactggct      1380
gactattcct ccattgcaga attcagcttt aggaacggtg aacacccctag ttttagagcc    1440 cagtctcaaa attagtccta acatccttac tctccccatc aggtcggggg gaggtgactg     1500
ttacactccc acttacctgt cagacctggc cgatgatgat gttaaactga gctccaatct     1560
tgtaatcctc ccgagtagaa acctccaata tgtgtcagca acctacgaca cctctagagt     1620
tgagcatgcc attgtatact atatctatag cgccgggcga ctatcatcgt attactaccc    1680
tgttaagttg cccataaagg gagatcctgt cagcctgcag ataggatgct tcccttgggg     1740
cctcaagcta tggtgccatc atttctgctc tgttatagat tcaggaactc gcaagcaggt    1800
cacccataca ggggcagtag ggattgagat cacttgcaat agcagatagc agtgtcttgg     1860
ccctacaaga tctcggagac cgggacccc aacagctgtg ggaccaggca ccgcgctgca     1920
ccatgcagac agctttcaat attaccatta t                                    1951
```

```
<210> SEQ ID NO 12
<211> LENGTH: 8
<212> TYPE: PRT
<213> ORGANISM: Artificial Sequence
<220> FEATURE:
<223> OTHER INFORMATION: Epitope tag

<400> SEQUENCE: 12

Asp Tyr Lys Asp Asp Asp Asp Lys
 1               5
```